United States Patent [19]
Amin et al.

[11] Patent Number: 5,919,775
[45] Date of Patent: Jul. 6, 1999

[54] METHOD FOR INHIBITING EXPRESSION OF INDUCIBLE NITRIC OXIDE SYNTHASE WITH TETRACYCLINE

[75] Inventors: Ashok R. Amin, Union, N.J.; Steven B. Abramson, Rye, N.Y.; Lorne M. Golub; Nungavaram S. Ramamurthy, both of Smithtown, N.Y.; Thomas F. McNamara, Port Jefferson, N.Y.; Robert A. Greenwald, Melville, N.Y.; Howard Trachtman, New Rochelle, N.Y.

[73] Assignees: The Research Foundation of The State University of New York, Stony Brook; Hospital For Joint Diseases, New York, both of N.Y.

[21] Appl. No.: 09/061,286

[22] Filed: Apr. 16, 1998

Related U.S. Application Data

[62] Division of application No. 08/697,815, Aug. 30, 1996, Pat. No. 5,789,395.

[51] Int. Cl.[6] .................................................. A61K 31/65
[52] U.S. Cl. ........................................................ 514/152
[58] Field of Search ............................................ 514/152

[56] References Cited

U.S. PATENT DOCUMENTS

| | | | |
|---|---|---|---|
| 5,216,025 | 6/1993 | Gross et al. | 514/565 |
| 5,246,970 | 9/1993 | Williamson et al. | 514/632 |
| 5,246,971 | 9/1993 | Williamson et al. | 514/634 |
| 5,266,594 | 11/1993 | Dawson et al. | 514/560 |
| 5,296,466 | 3/1994 | Kilbourn et al. | 514/6 |
| 5,358,969 | 10/1994 | Williamson et al. | 514/632 |
| 5,449,688 | 9/1995 | Wahl et al. | 514/546 |
| 5,468,630 | 11/1995 | Billiar et al. | 435/189 |
| 5,478,946 | 12/1995 | Murad et al. | 548/215 |
| 5,480,999 | 1/1996 | Chabrier De Lassauniere et al. | 548/500 |

OTHER PUBLICATIONS

Amin AR, Di Ceasre P, Vyas P, Attur M, Tzeng E, Billiar TR, Stuchin SA, and Abramson SB, *J Exp Med* 182:2097–2102 (1995a).

Amin AR, Vyas P, Attur M, Leszczynska–Piziak J, Patel IR, Weissman G, and Abramson SB, *Proc Natl Acad Sci USA* 92:7926–2930 (1995b).

Brinckerhoff CE, *Arthritis Rheum* 34:1073–1075 (1991).

Cao M, Westerhausen–Larson A, Niyibizi C, Kavalkovich K, Georgescu HI, Rizzo CF, Stefanovic–Racic M, and Evans CH, *42nd Ann Mtg Orthoped Res Soc,* p. 533 (1996).

Murrell GAC, Jang D, and Williams RJ, *Biochem Biophys Res Comm* 206:15–21 (1995).

Pfeilschifter J, Walker G, Eberhardt W, and Kunz D, *Endothelium 3* (suupl.), S51 (1995).

Schmidt HHHW and Walter U, *Cell* 78:919–925 (1994).

Vernillo AT, Ramamurthy NS, Lee HM, Mallya S, Auszmann J, Golub LM, and Rifkin BR, *J Dent Res* 73:367A (1993).

Vodovotz Y, Bogdan C, Paik J, Xie QW, and Nathan C, *J Exp Med* 178:605–613 (1993).

Vyas P, Attur M, Ou GM, Haines KA, Abramson SB, and Amin AR, p. 44 In *The Biology of Nitric Oixde,* Part 5, Moncada S, Stamler J, Gross S, and Higgs EA, eds., Portland Press Proceedings, (1996).

Yu LP Jr, Smith GN Jr, Hasty KA, and Brandt KD, *J Rheumatol* 18:1450–1452 (1991).

Ramamurthy N, Greenwald R, Moak S, Scuibba J, Goren A, Turner G, Rifkin B, and Golub L, "CMT/Tenidap treatment inhibits temporomandibular joint destruction in adjuvant arthritic rats," *Annals NY Acad Sci* 732:427–430 (1994).

Cole AA, Chubinskaya S, Chlebek K, Orth MW, Luchene LL, and Schmid TM, "Doxycycline inhibition of cartilage matrix degradation," *Annals NY Acad Sci* 732:414–415 (1994).

De Clerck YA, Shimada H, Taylor SM, and Langley KE, "Matrix metalloproteinases and their inhibitors in tumor progression," *Annals NY Acad Sci* 732:222–232 (1994).

Golub LM, Ramamurthy NS, and McNamara TF, "Tetracyclines inhibit connective tissue breakdown: New therapeutic implications for an old family of drugs," *Crit Rev Oral Biol Med* 2(2):297–322 (1991).

Golub LM, Suomalainen K, and Sorsa T, "Host modulation with tetracyclines and their chemically modified analogues," *Periodontol Restor Dent,* 80–90 (1992).

Greenwald RA, "Treatment of destructive arthritic disorders with MMP inhibitors," *Annals NY Acad Sci* 732:181–198 (1994).

Mallya SK, Hall JE, Lee HM, Roemer EJ, Simon SR, and Golub LM, "Interaction of matrix metalloproteinases with serine protease inhibitors," *Annals NY Acad Sci* 732:303–314 (1994).

Mitchell PG, Lopresti–Morrow L, Yocum SA, Sweeney FJ, and Reiter LA, "Inhibitiion of Interleukin–1–stimulated collagen degradation in cartilage explants," *Annals NY Acad Sci* 732:395–397 (1994).

(List continued on next page.)

*Primary Examiner*—Jon P. Weber
*Attorney, Agent, or Firm*—Hoffmann & Baron, LLP

[57] ABSTRACT

The invention is a method of inhibiting the production of nitric oxide (NO) in an in vivo, in vitro, or ex vivo biological system. The method employs a tetracycline compound to inhibit the production of NO and/or to inhibit the expression or activity of an inducible isoform of nitric oxide synthase (iNOS). Preferably, the tetracycline compound has inhibitory activity for metalloproteinases. Also it is preferred that the tetracycline compound is provided to the biological system in an amount which has little or no antibacterial activity in the system. Accordingly, preferred tetracycline compounds are tetracycline compounds which have be modified to reduce or eliminate their antimicrobial activity. The method can be used to treat medical conditions in mammals characterized by NO production mediated by iNOS, including, for example, inflammatory conditions.

10 Claims, 10 Drawing Sheets

OTHER PUBLICATIONS

Rifkin BR, Vernillo AT, Golub LM, and Ramamurthy NS, "Modulation of bone resorption by tetracyclines," *Annals Ny Acad Sci* 732:165–179 (1994).

Smith GN Jr, Brandt KD, and Hasty KA, "Procollagenase is reduced to inactive fragments upon activation in the presence of doxycycline," *Annals NY Acad Sci* 732:436–438 (1994).

Suomalainen K, Sorsa T, Golub LM, Ramamurthy N, Lee HM, Uitto VJ, Saari H, and Konttinen YT, "Specificity of the anticollagenase action of tetracyclines: Relevance to their anti–inflammatory potential," *Antimicrob Agents Chemother*, 36(1):227–229 (1992).

Uitto VJ, Firth JD, Nip L, and Golub LM, "Doxycycline and chemically modified tetracyclines inhibit gelatinase A (MMP–2) gene expression in human skin keratinocytes," *Annals NY Acad Sci* 732:140–151 (1994).

Yu LP Jr, Burr DB, Brandt KD, O'Connor BL, Rubinow A, and Albrecht M, "Effects of oral doxycycline administration on histomorphometry and dynamics of subchondral bone in a canine model of osteoarthritis," *J Rheumatol* 23(1):137–142 (1996).

Smith GN Jr, Brandt KD, and Hasty KA, "Activation of recombinant human neutrophil procollagenase in the presence of doxycycline results in fragmentation of the enzyme and loss of enzyme activity," *Arthit Rheum* 39(2):235–244 (1996).

Milano S, Arcoleo F, D'Agostino P, and Cillari E, "Intraperitoneal injection of tetracyclines protects mice from lethal endotoxemia downregulating inducible nitric oxide synthase in various organs and cytokine and nitrate secretion in blood," *Antimicrob Agents Chemother* 41(1):117–121 (1997).

Whiteman M, Kaur, H, and Halliwell B, "Protection against peroxynitrate dependent tyrosine nitration and $\alpha_1$–antiproteinase inactivation by some anti–inflammatory drugs and by the antibiotic tetracycline," *Annals Rheumatic Dis* 55(6):383–387 (1996).

Weller R, Pattullo S, Smith L, Golden M, Ormerod A, and Benjamin N, "Nitric oxide is generated on the skin surface by reduction of sweat nitrate," *J Investigative Dermatol* 107(3):327–331 (1996).

Tilley BC, Alarcón GS, Heyse SP, Trentham DE, Neuner R, Kaplan DA, Clegg DO, Leisen JCC, Buckley L, Cooper SM, Duncan H, Pillemer SR, Tuttleman M, and Fowler SE, "Minocycline in rheumatoid arthritis," *Annals Intern Med* 122(2):81–89 (1995).

Stefanovic–Racic M, Meyers K, Meschter C, Coffey JW, Hoffman RA, and Evans CH, "N–Monomethyl arginine, an inhibitor of nitric oxide synthase, suppresses the development of adjuvant arthritis in rats," *Arthrit Rheum* 37(7):1062–1069 (1994).

Sakurai H, Kohsaka H, Liu MF, Higashiyama H, Hirata Y, Kanno K, Saito I, and Miyasaka N, "Nitric oxide production and inducible nitric oxide sythase expression in inflammatory arthritides," *J Clin Invest* 96:2357–2363 (1995).

McCartney–Francis N, Allen JB, Mizel DE, Albina JE, Xie QW, Nathan CF, and Wahl SM, "Suppression of arthritis by an inhibitor of nitric oxide synthase," *J Exper Med* 178:749–754 (1993).

Pipili–Synetos E, Sakkoula E, and Maragoudakis ME, "Nitric oxide is involved in the regulation of angiogenesis," *Br J Pharmacol* 108(4):855–857 (1993).

Pipili–Synetos E, Sakkoula E, Haralabopoulos G, Andriopoulou P, Peristeris P, and Maragoudakis ME, "Evidence that nitric oxide is an endogenous antiangiogenic mediator," *Br J Pharamol* 111(3):894–902 (1994).

Maragoudakis ME, Peristeris P, Missirlis E, Aletras A, Andriopoulou P, and Haralabopoulos G, "Inhibition of angiogenesis by anthracyclines and titanocene dichloride," *Annals NY Acad Sci,* 732:280–293 (1994).

Kasten, TP, Collin–Osdoby P, Patel N, Osdoby P, Krukowski M, Misko TP, Settle SL, Currie MG, and Nickos GA, "Potentiation of osteoclast bone–resorption activity by inhibition of nitric oxide synthase," *Proc Natl Acad Sci USA* 91(9):3569–3573 (1994).

Farias–Eisner R, Sherman MP, Aeberhard E, and Chaundhuri G, "Nitric oxide is an important mediator for tumoricidal activity in vivo," *Proc Natl Acad Sci USA,* 91(20):9407–9411 (1994).

Taskiran D, Stefanovic–Racic M, Georgescu H, and Evans C, "Nitric oxide mediates suppression of cartilage proteoglycan synthesis by Interleukin–1," *Biochem Biophys Res Commun* 200(1):142–148 (1994).

Yu LP Jr, Smith GN Jr, Brandt KD, Myers SL, O'Connor BL, and Brandt DA, "Reduction of the severity of canine osteoarthritis by prophylactic treatment with oral doxycycline," *Arthrit Rheum* 35(10):1150–1159 (1992).

Golub et al. (1987a) J. Dent Res., 66(8), "A Non–Antibacterial Chemically–Modified Tetracycline Inhibits Mammalian Collagenase Activity", pp. 1310–1314.

Golub et al. (1991) Crit. Rev. Oral Biol. Pat., 2(3), "Tetracyclines Inhibit Connective Tissue Breakdown: New Therapeutic Implications for an Old Family of Drugs", pp. 297–321.

Vernillo et al. (1994) Curr. Opin. Periodon., "The Nonantimicrobial Properties of Tetracyclines for the Treatment of Periodontal Disease", pp. 111–118.

Webster et al. (1994) Arch. Dermatol., 130(6), "Inhibition of a Model of in vitro Granuloma Formation by Tetracyclines and Ciprofloxacin. Involvment of Protein Kinase C", pp. 748–752.

Weller et al. (1996) J. Invest. Dermatol. 107(3), "Nitric Oxide is Generated on the Skin Surface by Reduction of Sweat Nitrate", pp. 327–331.

Shapira et al. (1996) Infect. Immun., 64(3), "Protection Against Endotoxic Shock and Lipopolysaccharide–Induced Local Inflammation by Tetracycline: Correlation with Inhibition of Cytokine Secretion", pp. 825–828.

Greenwald et al. (1987) J. Rheumatol., 14(1), "Tetracyclines Inhibit Human Synovial Collagenase in vivo and in vitro", pp. 28–32, in Medline An 87198535.

Breedveld et al. (1990) J. Rheutamol., 17(1), "Minocycline Treatment for Rheumatoid Arthritis: An Open Dose Finding Study", pp. 43–46.

Rifkin et al. (1993) J. Periodontal., 64(8Suppl), "Blocking Periodontal Disease Progression by Inhibiting Tissue–Destructive Enzymes: A Potential Therapeutic Role for Tetracyclines and Their Chemically–Modified Analogs", pp. 819–827.

Rifkin et al. (Sep. 6, 1994) Ann. New York Acad. Sci., 732, "Modulation of Bone Resorption by Tetracyclines", pp. 165–180.

Golub et al. (1994) Ann. New York Acad. Sci., 732, "A Non–Antimicrobial Tetracycline Inhibits Gingival Matrix Metalloproteinases and Bone Loss in Porphyromonas Gingivalis–Induced Periodontitis in Rats", pp. 96–111.

Whiteman et al. (1996) Ann Pheum. Dis., 55(6), "Prevention Against Peroxynitrate–Dependent Tyrosine Nitration and Inactivation of α1–Antiproteinase by Some Anti–Inflammatory Drugs and by the Antibiotic Tetracycline", pp. 383–387, in CAPLUS AN 1996: 460684.

Amin et al. (1996a) Arthritis Rheum., 39(9 Suppl.), "A Novel Mechanism of Action of Tetracyclines: Inhibitory Effects of Nitric Oxide Synthase Activity in Osteoarthritis", p. S211, in DRUGU AN 96–44053.

Trachtman et al. (1996) Biochem. Biophys. Res. Comm., 229(1), "Chemically Modified Tetracyclines Inhibit Inducible Nitric Oxide Synthase Expression and Nitric Oxide Production in Cultured Rat Mesangial Cells", pp. 243–348.

Amin et al. (1996) Proc. Natl. Acad. Sci., USA, 93, "A Novel Mechanism of Action of Tetracyclines: Effects on Nitric Oxide Synthases", pp. 14014–14019.

Milano et al. (1997) Antimicrob. Agents Chemother., 41(1), "Intraperitoneal Injection of Tetracyclines Protects Mice from Lethal Endotoxemia Downregulating Inducible Nitric Oxide Synthase in Various Organs and Cytokine and Nitrate Secretion in Blood", pp. 117–121.

Amin et al. (1997) J. Invest. Med., 45(3), "Chemically Modified Tetracyclines (CMTs) That lack Antimicrobial Activity Inhibit Expression of Inducible Nitric Oxide Synthase in Murine Macrophages", p. 237A.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:1:

ACGGAGAAGC TTAGATCTGG AGCAGAAGTG      30

(2) INFORMATION FOR SEQ ID NO:2:

(i) SEQUENCE CHARACTERISTICS:

```
            (A) LENGTH: 30 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:2:

CTGCAGGTTG GACCACTGGA TCCTGCCGAT                                30

(2) INFORMATION FOR SEQ ID NO:3:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (ix) SEQUENCE DESCRIPTION: SEQ ID NO:3:

TCCTTCGTTG CCGGTCCACA                                           20

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:4:

CGTCTCCGGA GTCCATCACA                                           20
```

METHOD FOR INHIBITING EXPRESSION OF INDUCIBLE NITRIC OXIDE SYNTHASE WITH TETRACYCLINE

This application is a division of Ser. No. 08/697,815, filed Aug. 30, 1996, now U.S. Pat. No. 5,789,395.

BACKGROUND OF THE INVENTION

The invention relates to methods of reducing the generation of nitric oxide in biological systems. More specifically, the invention relates to the inhibition of inducible nitric oxide synthase in mammals.

Nitric oxide (hereinafter NO) is a recently recognized multifunctional mediator that is produced by and acts on various cells, and that participates in inflammatory and autoimmune-mediated tissue destruction. NO production is catalyzed by a family of ubiquitous enzymes called nitric oxide synthases (also nitric oxide synthetase, hereinafter NOS). NOS is a naturally expressed enzyme in mammals which catalyzes the mixed functional oxidation of L-arginine (a common amino acid) to L-citrulline and nitric oxide. The enzyme removes a guanidino nitrogen of L-arginine to form the nitric oxide. Several isoforms of the NOS enzyme have been identified, and they are generally divided into two types: constitutive NOS (hereinafter cNOS) and inducible NOS (hereinafter iNOS). Additional details concerning types and functions of some NOS enzymes are found, for example, in U.S. Pat. Nos. 5,478,946 and 5,468,630, the entire disclosures of which are incorporated herein by reference. A cDNA clone capable of expressing a human inducible NOS has been described in U.S. Pat. No. 5,468,630.

The nitric oxide product of the NOS enzymes appears to function as either a signaling or an effector molecule depending on the isoform of the NOS enzyme which is involved in its formation. The constitutive form of NOS produces small amounts of NO, which activate guanylate cyclase resulting in the formation of cyclic guanosine monophosphate (cGMP). The cGMP, in turn, mediates several specific functions, including endothelium-dependent vascular relaxation and neural transmission. By contrast, NO is produced in much larger quantities by the inducible isoforms of the enzyme, designated inducible nitric oxide synthases (iNOS). NO produced by an iNOS appears to mediate the cytotoxic activity of macrophages. Other cells which produce iNOS include endothelial cells, neutrophils, Kupffer cells and hepatocytes, and murine fibroblasts stimulated with cytokines. NO is also a chemical messenger in the brain, and appears to be produced there by a separate NOS isoform.

Several physiological activities have been ascribed to NO. Vasoactive agents such as histamine and bradykinin stimulate NO production. NO is a potent vasodilator that increases blood flow and vascular permeability. Interleukin-1 (IL-1) induces the expression of iNOS in pancreatic islets. NO appears to be a mediator of the inhibitory effects of IL-1 on islet function. Another inducer of iNOS is bacterial endotoxin, indicating that NO is involved as a mediator of endotoxic or septic shock. Other inducers of the enzyme include gamma interferon, tumor necrosis factor and other inflammatory cytokines (Collier et al. 1989). For example, tumor necrosis factor appears to be involved in the systemic hypotension associated with septic shock.

NOS is also overexpressed (expressed in increased and often abnormal amounts) in a variety of inflammatory tissues, leading some to postulate that the modulation of NO synthesis and action could represent a new approach to the treatment of inflammatory and autoimmune conditions (Vane et al. 1994, Schmidt et al. 1994). Vane and co-workers have implicated NO as an important mediator of inflammation in animal models (Vane et al. 1994). Where examined, NO formation is found to be increased in autoimmune diseases (rheumatoid arthritis, systemic lupus erythematosus, ulcerative colitis, Crohn's disease), and several classic inflammatory symptoms (erythema, vascular leakiness) are reversed by NOS inhibitors (Schmidt et al. 1994, Nathan et al. 1994, Marletta 1994). The most compelling evidence for NO as a mediator of tissue injury has been found in studies of arthritis, including studies carried out in animal models of that disease (McCartney-Francis et al. 1993, Stefanovic-Racic et al. 1994), as well as studies of human osteoarthritis (OA) (Amin et al. 1995a) and rheumatoid arthritis (RA) (Sakurai et al. 1995).

It has recently been observed that human OA-affected cartilage can spontaneously release NO under ex vivo conditions in quantities sufficient to cause cartilage damage (Amin et al. 1995a). An inducible NOS, designated "osteoarthritis-affected NOS" (OA-NOS), is overexpressed in OA-affected cartilage, but is not detectable in normal cartilage. The inducible OA-NOS has properties similar to neuronal NOS (based on its molecular weight and antibody cross-reactivity among α-NOS antibodies) and the 133 kD iNOS (sensitive to NF-κB and cycloheximide, upregulated by IL-1β+TNFα+LPS). NO is known to potentiate matrix degradation, which includes inhibition of proteoglycan and collagen type II synthesis (Taskiran et al. 1994, Cao et al. 1996) and upregulation of metalloproteinase activity (Murrell et al. 1995).

Several inhibitors of nitric oxide synthase have been identified. Most of these inhibitors are derivatives of L-arginine, the natural substrate of the NOS enzymes. For example, $N^G$-methyl-L-arginine and L-$N^\omega$-nitroarginine are competitive inhibitors of NO synthesis. U.S. Pat. No. 5,358,969 describes the inhibition of NO formation in acute or chronic inflammatory diseases. The method includes administering to a mammal an NO-inhibitory amount of a methyl-, 1,1-dimethyl-, or amino-substituted guanidine compound. See also U.S. Pat. Nos. 5,246,970 and 5,246,971.

U.S. Pat. No. 5,216,025 describes the use as NO inhibitors for potentiating pressor agents in certain hypotensive patients. These inhibitors include $N^G$-substituted arginines in which a hydrogen on the guanidino amino group of arginine is replaced by another atomic or molecular species.

U.S. Pat. No. 5,478,946 discloses unsaturated guanidino compounds which are said to regulate nitric oxide synthase and to thereby indirectly regulate levels of cGMP. These compounds can include a variety of substituents, including $C_6$–$C_{12}$ aryl groups, at various sites in the unsaturated guanidino backbone.

U.S. Pat. No. 5,480,999 discloses compounds of the structure AB, in which A is a cyclooxygenase inhibitor having an accessible acid function, and B is an arginine analog. The compounds are said to have mixed cyclooxygenase- and NOS-inhibitory activity in the same structure.

The production of nitric oxide can also be inhibited in other ways. For example, NO production can be inhibited by means of a compound which interferes with the activity of a cofactor of iNOS, such as tetrahydrobiopterin. Alternatively, net production of NO can be reduced by means of a nitric oxide scavenger. Compounds said to be suitable for use in these kinds of methods are disclosed, for example, in U.S. Pat. No. 5,449,688, the entire disclosure of which is incorporated herein by reference. Tetrahydrobiopterin synthesis inhibitors include, for example, 2,4-diamino-6-hydroxy-pyrimidine. NO scavengers include, for example, hemoglobin and diethyldithiocarbamate (DETC).

Tetracycline and a number of chemical derivatives thereof form a particularly successful class of antibiotics. Certain of the tetracycline compounds, including tetracycline itself, as well as sporocycline, etc., are broad spectrum antibiotics, having utility against a wide variety of bacteria. The parent compound, tetracycline, has the following general structure:

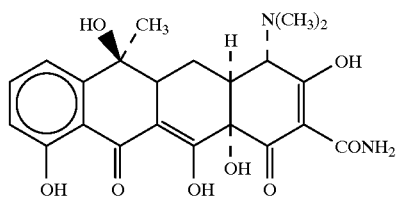

The numbering system of the multiple ring nucleus is as follows:

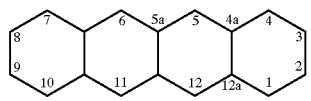

Tetracycline, as well as the 5-OH (terramycin) and 7-Cl (aureomycin) derivatives, exist in nature, and are all well known antibiotics. Natural tetracyclines may be modified without losing their antibiotic properties, although certain elements of the structure must be retained to do so. The modifications that may and may not be made to the basic tetracycline structure have been reviewed by Mitscher (1978). According to Mitscher, the modification at positions 5–9 of the tetracycline ring system can be made without causing the complete loss of antibiotic properties.

However, changes to the basic structure of the ring system, or replacement of substituents at positions 1–4 or 10–12, generally lead to synthetic tetracyclines with substantially less, or essentially no, antibacterial activity. For example, 4-dedimethylaminotetracycline is commonly considered to be a non-antibacterial tetracycline.

During recent years it has been established that tetracyclines, which are rapidly absorbed and have a prolonged half-life, exert biological effects independent of their antimicrobial activity (Golub et al. 1991, Golub et al. 1992, Uitto et al. 1994). Such effects include inhibition of matrix metalloproteinases, including collagenase (MMP-1), gelatinase (MMP-2) and stromelysin (MMP-3), as well as prevention of pathogenic tissue destruction (Golub et al. 1991). In inflammatory arthritides such as rheumatoid arthritis (RA), these matrix metalloproteinases have been identified in homogenates and cultures of rheumatoid synovium, detected in inflammatory synovial fluids and localized immunologically and by in situ hybridization in proliferative pannus and synovium (Brinckerhoff 1991). These metalloproteinases are known to be upregulated in OA-affected joints (Greenwald 1994, Mohtai et al. 1993). Interestingly, Yu et al. (1992) have also shown that prophylactic administration of doxycycline markedly reduced the severity of OA in dog models. To assess the safety and efficacy of minocycline (a semisynthetic tetracycline) in the treatment of arthritis, a double-blind, randomized, multicenter trial indicated that the drug was safe and effective for patients with mild and moderate arthritis (Tilley et al. 1995). Furthermore, recent studies have also suggested that tetracyclines and inhibitors of metalloproteinases inhibit tumor progression (DeClerck et al. 1994), bone resorption (Rifkin et al. 1994) and angiogenesis (Maragoudakis et al. 1994), and may have anti-inflammatory properties (Ramamurthy et al. 1994).

However, the use of tetracycline antibiotics, while generally effective for treating infection, can lead to undesirable side effects. For example, the long term administration of antibiotic tetracyclines can reduce or eliminate healthy flora, such as intestinal flora, and can lead to the production of antibiotic resistant organisms or the overgrowth of yeast and fungi. Accordingly, chemically-modified tetracyclines, in which the antimicrobial activity is attenuated or deleted, can be preferred for use in applications in which anti-collagenolytic activity is indicated.

In view of the above considerations, it is clear that there is a need to supplement existing methods of inhibiting nitric oxide production with new methods in which specific and efficient compounds can be used to effect prompt and selective reductions in the clinical consequences associated with excessive nitric oxide levels.

Accordingly, it is one of the purposes of this invention to overcome the above limitations in the identification and use of inhibitors of nitric oxide production, by providing a new class of inhibitors of nitric oxide. The new inhibitors appear to inhibit production of NO specifically and with relatively high activity. Moreover, the class of inhibitors has the advantage of already being approved for use in humans for other purposes, implying significant prospects for their rapid adoption in the clinical setting. Other advantages and purposes will readily present themselves to the skilled practitioner.

SUMMARY OF THE INVENTION

It has now been discovered that these and other objectives can be achieved by the present invention, which provides a method for inhibiting nitric oxide production or nitric oxide synthase expression or activity in a biological system by providing a tetracycline compound to the system in an amount which is effective to achieve the specified result.

Preferably, the method employs a tetracycline compound which has substantially no anti-microbial activity at the level being provided to the system. It is further preferred that the tetracycline compound has metalloproteinase inhibitory activity. Highly preferred tetracycline compounds include 6-demethyl-6-deoxy-4-dedimethylaminotetracycline (CMT-3), 6-α-deoxy-5-hydroxy-4-dedimethylaminotetracycline (CMT-8), 4-dedimethylaminotetracycline (CMT-1), doxycycline, or minocycline.

In one embodiment, the method includes providing to the biological system an amount of a tetracycline compound sufficient to cause a decrease in the amount of nitric oxide produced therein.

Preferably, the biological system is a mammal having a condition characterized by increased nitric oxide production in a tissue. The method is particularly suitable for use in a biological system which is a mammal having a condition characterized by an abnormally high level of activity of inducible nitric oxide synthase in a tissue. Such conditions capable of treatment by means of the method of the invention include, for example, inflammatory diseases such as nitric oxide-dependent glomerular inflammation and osteoarthritis.

The method can further include providing to the biological system an anti-inflammatory amount of a steroidal or non-steroidal anti-inflammatory drug.

The method can also be employed in cases wherein the biological system is an in vitro cellular system or an ex vivo tissue or organ system, and wherein a measured amount of nitric oxide production is indicative of expression or activity of inducible nitric oxide synthase.

In another embodiment, the invention is a method for treating a mammal having an inflammatory condition, comprising administering to the mammal an amount of a tetracycline compound sufficient to inhibit nitric oxide production in the mammal. The inflammatory condition can be an acute inflammatory condition or a chronic inflammatory condition.

In another embodiment, the invention is a method of inhibiting expression or activity of inducible nitric oxide synthase in a biological system, including administering to the biological system an amount of a tetracycline compound sufficient to inhibit inducible nitric oxide synthase expression or activity therein.

Accordingly, the invention provides new methods of inhibiting nitric oxide production in in vivo, in vitro, and ex vivo biological systems. New clinical treatment protocols are possible using this new method, to reduce or eliminate nitric oxide production (and consequent pathology), especially by interfering with expression of inducible nitric oxide synthases. A variety of diseases and conditions characterized by increased NO production or overexpression of iNOS can be treated by administering a tetracycline compound as described herein. New assay methods capable of revealing the amount of NO production or the amount of iNOS expression or activity are also provided.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein.

DETAILED DESCRIPTION OF THE PREFERRED EMBODIMENTS

Figure 1A:
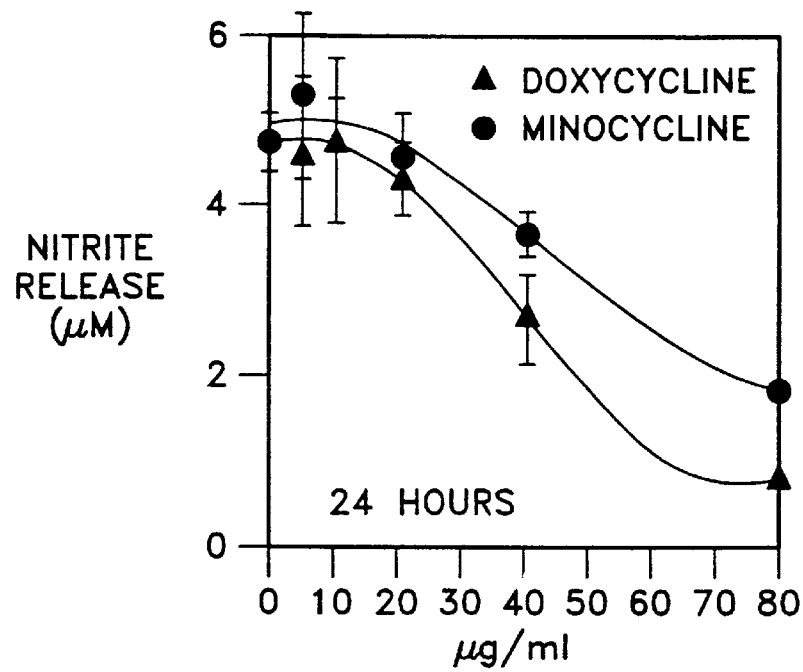
FIGS. 1A–1C are a time series of graphs illustrating dose-dependent inhibition of nitric oxide production in articular cartilage organ culture by doxycycline and minocycline.

The present invention is directed to a method for inhibiting nitric oxide (NO) production in in vitro, in vivo, and ex vivo biological systems. The method can be adapted for use in assay systems, e.g., assaying NO production or iNOS expression or activity in cells. Preferably, the method is employed to inhibit NO production in living animals, such as mammals. In particular, the method provides a means for protecting mammals against pathology and other consequences associated with or mediated by increased or excessive NO production in inflammatory diseases and other conditions. The method includes the use of tetracycline compounds as inhibitors of nitric oxide production and/or inducible nitric oxide synthase expression or activity.

The invention has been developed based on the unexpected observation by Applicants that tetracycline compounds inhibit the production of nitric oxide mediated by inducible nitric oxide synthase. It is known that tetracycline compounds inhibit matrix metalloproteinases such as collagenase. However, inducible nitric oxide synthase is not a metalloproteinase, and the relationship between iNOS activity and collagenase activity, if any, remains to be identified. Applicants are also unaware of any, physiological or biochemical basis for expecting that tetracyclines would inhibit the production of nitric oxide in systems capable of expressing iNOS. It is, therefore, surprising that tetracycline compounds having anti-metalloproteinase activity would also be found to have significant NO-production inhibitory activity. What is still more surprising is that the relative potencies of the tetracycline compounds as inhibitors of collagenases appears to be mirrored by a similar hierarchy in their relative potencies as inhibitors of NO production. Applicants are not presently aware of any theoretical basis which might explain this unexpected correspondence, but believe that the observation itself may carry significant therapeutic implications for a variety of diseases believed to be associated with or characterized by elevated nitric oxide production, and may help to predict courses of treatment.

The present invention can be performed using an in vitro, ex vivo, or in vivo biological system. The term "biological system" is used herein to refer to the types of systems, including in vitro, in vivo, and ex vivo systems, in which the method can be practiced. For example, the method can be used in living mammals (in vivo), as well as in cultured cellular systems (in vitro) and cultured organ systems (ex vivo). In vivo practice of the invention permits application in the relief or palliation of medical and veterinary diseases, conditions, and syndromes. Other uses include assay systems which can be used in the laboratory for experimental or clinical application.

The medical or veterinary conditions treatable by means of the present invention occur in mammals. Mammals include, for example, humans, as well as pet animals such as dogs and cats, laboratory animals such as rats and mice, and farm animals, such as horses and cows.

The present invention is directed to the prevention or treatment of a broad spectrum of diseases which may be linked to the production of nitric oxide by inducible nitric oxide synthase by cells such as leukocytes (e.g., neutrophils and macrophages) and other cells. In particular, the method of the invention is useful in reducing or inhibiting conditions in which NO production is increased substantially over usual levels in a system, including both normal and abnormal increases.

The invention is particularly illustrated herein in reference to treatment of inflammatory diseases, specifically in reference to glomerulonephritis and osteoarthritis. In these illustrative treatments, standard state-of-the-art in vitro and ex vivo models have been used. For example, Applicants have used a model in which NO production is induced by treating rat mesangial cells with gamma interferon (γIFN). Applicants have also used other models in which NO production is increased, such as in OA-affected cartilage or lipopolysaccharide-stimulated murine macrophages. These methods can be used to identify agents which can be expected to be efficacious in in vivo treatment regimens. However, it will be understood that the method of the invention is not limited to the treatment of nephritis and osteoarthritis, but to a variety of other diseases in which NO production or iNOS expression or activity plays a role.

For example, NO appears to be involved in various medical conditions, including, for example, malaria, senescence, diabetes, as well as vascular stroke and neurodegenerative disorders such as Alzheimer's disease and Huntington's disease. NO also appears to be involved in cardiac disease, including re-perfusion-associated injury following infarction wherein neutrophils have been found to attack the heart muscle. Furthermore, induction of NO synthesis in pancreatic islets contributes to the onset of juvenile diabetes. Since many of these conditions are characterized by alterations in cytokine expression, it may well be that abnormally high expression or activity of inducible NOS is a key factor in the associated pathology. The invention can be used to treat any of these diseases.

A major class of diseases which can be treated by means of the invention are diseases characterized by inflammation. Inflammation is generally recognized as being roughly divisible into two broad categories of conditions: acute inflammation and chronic inflammation. Acute inflammation is generally of relatively short duration, lasting for from about a few minutes to about one to two days. Its main characteristics are increased blood flow, exudation of fluid and plasma proteins (edema) and emigration of leukocytes, predominantly neutrophils. Chronic inflammation is of longer duration, e.g., days to weeks or even longer, and is associated histologically with the presence of lymphocytes and macrophages and with proliferation of blood vessels and connective tissue. See, e.g., Cotran et al. (1989), Chandrasoma & Taylor (1991).

Inflammation is manifested by heat, redness, swelling, pain and loss of function. The causes of inflammation are numerous and include such factors as microbial infections (e.g., bacterial and fungal infections), physical agents (e.g., burns, radiation, and trauma), chemical agents (e.g., toxins and caustic substances), tissue necrosis and various types of immunologic reactions. NO is believed to be one of a number of reactive products produced in the immune and inflammatory responses to such insults. In particular, elevated levels of NO production common to chronic inflammation are a likely contributor to the non-specific tissue destruction often seen in such conditions.

Inflammatory conditions treatable by means of the present invention include, for example, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Accordingly, the method of the invention can be used to prevent, inhibit, or alleviate such NO-related conditions. The method of the invention can be used to prevent, inhibit, or alleviate any condition in which overexpression of inducible NOS is involved.

The method involves the providing or administering a tetracycline compound in an amount which is effective for reducing nitric oxide production in a biological system. The inhibition may result from a down-regulation of the expression or activity of inducible nitric oxide synthase. For example, Applicants have found that doxycycline (and other tetracycline compounds) appears to inhibit transcription of iNOS in cell culture. Such reduced expression of the enzyme will typically result in reduced NO production in the tissue.

The amount of the tetracycline compound used according to the invention is an amount that is effectively inhibitory of iNOS expression or activity. An amount of a tetracycline compound is effectively inhibitory of iNOS if it significantly reduces iNOS expression or activity, or if it reduces NO production.

Preferably, the tetracycline compound is provided in an amount which has little or no antimicrobial activity. A tetracycline compound is not effectively antimicrobial if it does not significantly prevent the growth of microbes. Accordingly, the method can beneficially employ a tetracycline compound which has been modified chemically to reduce or eliminate its antimicrobial properties. The use of such chemically-modified tetracyclines is preferred in the present invention since they can be used at higher levels than antimicrobial tetracyclines, while avoiding certain disadvantages, such as the indiscriminate killing of beneficial microbes, and the emergence of resistant microbes, which often accompanies the use of antimicrobial or antibacterial amounts of such compounds.

The invention can also use tetracycline compounds which possess antibacterial activity. However, such compounds are preferably employed in an amount which has substantially no anti-bacterial effect but which is effective for inhibiting iNOS activity in the involved tissue. Preferred compounds of this type include tetracycline, doxycycline, demeclocycline, and minocycline.

The tetracycline compounds useful according to the method of the invention appear to exhibit their beneficial effect in a dose-dependent manner. Thus, within broad limits, administration of larger quantities of a tetracycline compound has been observed to inhibit iNOS activity to a greater degree than does administration of a smaller amount. Moreover, efficacy has been observed at dosages below the level at which toxicity is seen.

The maximal dosage for a subject is the highest dosage which does not cause undesirable or intolerable side effects. For example, the tetracycline compound can be administered in an amount of from about 0.1 mg/kg/day to about 30 mg/kg/day, and preferably from about 1 mg/kg/day to about 18 mg/kg/day. For the purpose of the present invention, side effects may include clinically significant antimicrobial or antibacterial activity, as well as toxic effects. For example, a dose in excess of about 50 mg/kg/day would likely produce side effects in most mammals, including humans. In any event, the practitioner is guided by skill and knowledge in the field, and the present invention includes without limitation dosages which are effective to achieve the described phenomena.

Preferred chemically-modified tetracyclines are those which lack the dimethylamino group at position 4 of the ring structure. Such chemically-modified tetracyclines include, for example, 4-dedimethylaminotetracycline (CMT-1), 4-dedimethylamino-5-oxytetracycline, 4-dedimethylamino-7-chlorotetracycline (CMT-4), 4-hydroxy-4-dedimethylaminotetracycline (CMT-6), 5a,6-anhydro-4-hydroxy-4-dedimethylaminotetracycline, 6-demethyl-6-deoxy-4-dedimethylaminotetracycline (CMT-3), 4-dedimethylamino-12a-deoxytetracycline (CMT-7), and 6-α-deoxy-5-hydroxy-4-dedimethylaminotetracycline (CMT-8). Also, tetracyclines modified at the 2 carbon position to produce a nitrile, e.g., tetracyclinonitrile, are useful as non-antibacterial, anti-iNOS agents.

Further examples of tetracyclines modified for reduced antimicrobial activity include 6-α-benzylthiomethylenetetracycline, the mono-N-alkylated amide of tetracycline, 6-fluoro-6-demethyltetracycline, or 11α-chlorotetracycline.

Particularly preferred tetracycline compounds suitable for use according to the invention include 6-demethyl-6-deoxy 4-dedimethylaminotetracycline (CMT-3), 6-α-deoxy-5-hydroxy-4-dedimethylaminotetracycline (CMT-8), 4-dedimethylaminotetracycline (CMT-1), doxycycline, and minocycline.

In certain cases, tetracycline compounds having only limited biodistribution may be preferred for localized activity. CMT-2, CMT-6, and other CMTs exhibiting such substantially local distribution are preferred for their localized efficacy in inhibiting iNOS activity at a site of injury, without exhibiting broader systemic inhibition. For example, the topical application of these non-absorbable CMTs would be desirable in oral lesions, since the CMTs would not be absorbed to any significant degree even if swallowed.

Topical application of tetracycline compounds in amounts of up to about 25% (w/w) in a vehicle are therefore appropriate depending upon indication. More preferably, application of tetracycline compounds in amounts of from about 0.1% to about 10% is believed to effectively inhibit iNOS according to the invention. It is believed that these quantities do not induce significant toxicity in the subject being treated.

Combined or coordinated topical and systemic administration of tetracycline compounds is contemplated under the invention. For example, a non-absorbable tetracycline compound, such as CMT-2 or CMT-6, can be administered topically, while a tetracycline compound capable of substantial absorption and effective systemic distribution in the subject, such as CMT-1, CMT-3, CMT-7, or CMT-8, is administered systemically.

The tetracycline compound can also be administered with an adjunct agent capable of inhibiting inflammation in tissue. Preferred anti-inflammatory agents capable of co-administration include steroidal, and preferably non-steroidal anti-inflammatory drugs (NSAIDs). Suitable NSAIDs can be selected from the various classes of such compounds. Such classes include, for example, salicylates such as acetylsalicylic acid and diflunisal; acetic acids such as indomethacin, sulindac, tolmetin, diclofenac, and etodolac; propionic acids such as flurbiprofen, naproxen, and ketoprofen; and fenamates such as meclofenamate; and oxicams such as piroxicam. Generally, the amount of the NSAID is an amount sufficient to inhibit inflammation in the affected tissue. The anti-inflammatory amount will depend on the NSAID being employed and other understood factors, and can be readily determined by the skilled practitioner.

The preferred pharmaceutical composition for use in the method of the invention includes a combination of the tetracycline compound in a suitable pharmaceutical carrier (vehicle) or excipient as understood by practitioners in the art. Parenteral administration (e.g., intravenous injection) is a preferred route of delivery of the tetracycline, and compositions including the tetracycline compound with appropriate diluents, carriers, and the like are readily formulated. Enteral use is also contemplated, and formulations such as tablets can be employed to provide the compound. Alternatively, delivery of the tetracycline compound can include topical application. Accordingly, the carrier is preferably suited for topical use. Compositions deemed to be suited for such topical use include as gels, salves, lotions, ointments and the like. The non-antimicrobial amount of the tetracycline compound may be incorporated with a support base or matrix or the like to provide a pre-packaged surgical or burn dressing or bandage which can be directly applied to skin.

The following examples are provided to assist in a further understanding of the invention. The particular materials and conditions employed are intended to be further illustrative of the invention and are not limiting upon the reasonable scope thereof.

EXAMPLE 1

Renal mesangial cells were cultured in media containing 50 U/mL gamma interferon (IFN-γ) and 10 μg/mL bacterial lipopolysaccharide (LPS). Test media contained either (a) no further additives; (b) CMT-5, a tetracycline derivative having no appreciable anti-collagenase activity; (c) CMT-1, a tetracycline derivative having modest anti-collagenase activity; or (d) CMT-3 and CMT-8, derivatives having a high level of anti-collagenase activity. The CMT additives were included at concentrations of 1, 2.5, 5, and 10 μ/mL. NO production was assayed by the Greiss reaction, and iNOS content was measured by Western analysis.

Exposure of the renal mesangial cells to CMT-3 and CMT-8 resulted in a time-dependent inhibition of NO production from 24–72 hr. At 48 hr, the effect was maximal (>80%) at a drug concentration of 5 μg/mL ($P<0.01$). Incubation of the cells with CMT-1 caused less pronounced inhibition of NO production after 48 hr, (~60% of control) despite higher drug concentration (10 μg/mL). Changes in NO production were paralleled by alterations in cellular iNOS content, measured by Western analysis, after exposure to the tetracycline compounds, at 5 μg/mL for 48 hr. CMT-5, however, had no discernable effect on NO production or iNOS expression.

The use of IFN-γ to induce renal injury is a model of glomerulonephritis known in the art. Glomerulonephritis is characterized by increased production of NO. The skilled artisan, therefore, will appreciate the capacity of this model for demonstrating methods for the inhibition of NO production. The results presented above clearly show that certain chemically modified tetracycline compounds, namely those having anti-collagenolytic activity, are capable of inhibiting NO production in renal mesangial cells. More specifically, these compounds are effective to inhibit iNOS protein synthesis in these cells. At a minimum, therefore, these agents will be useful in the treatment of NO-dependent glomerular inflammation. More generally, however, the utility of these compounds in the glomerulonephritis model implies NO-production inhibitory activity for these compounds in other biological systems and other pathological conditions characterized by abnormal NO production.

EXAMPLES 2–6

We evaluated the action of tetracycline compounds on the spontaneous release of nitric oxide from osteoarthritis-affected human cartilage in ex vivo conditions and on iNOS activity in lipopolysaccharide-stimulated murine macrophages. Both of these enzyme isoforms have shown distinct susceptibility to pharmacologic intervention by hydrocortisone and TGF-β in vitro (Amin et al. 1995a). As described in Examples 2–6 below, we have now found that (a) doxycycline and minocycline both inhibit the activity of iNOS (minocycline ≧doxycycline) and inducible OA-NOS (doxycycline>minocycline); (b) doxycycline and minocycline inhibit iNOS expression at the level of iNOS mRNA and protein expression, thereby downregulating its specific activity; and (c) unlike acetylating agents or competitive inhibitors of iNOS (i.e., analogs of L-arginine), doxycycline and minocycline do not directly inhibit the catalytic activity of iNOS in vitro in an L-arginine-to-L-citrulline conversion assay.

EXAMPLE 2
Effect of Tetracyclines on Inducible OA-NOS Expression in Human OA-affected Cartilage We examined whether tetracyclines, e.g., doxycycline or minocycline, could block human OA-NOS activity under ex vivo conditions. Generally accepted pharmacologically relevant concentrations were selected for this study based on previous reports (Greenwald 1994, Yu et al. 1991, Cole et al. 1994, Mallya et al. 1994). OA-affected cartilage was obtained from patients with advanced OA undergoing knee replacement surgery and free of steroidal/nonsteroidal anti-inflammatory drugs for at least 2 wk before surgery. OA-affected cartilage slices (FIGS. 1A–1C) were incubated in 0.1% BSA/endotoxin-free medium with 5–80 μg/mL of doxycycline or minocycline (Sigma Chemical Co., St. Louis, Mo.) for 24, 48 and 72 h in ex vivo conditions.

Figure 1B:
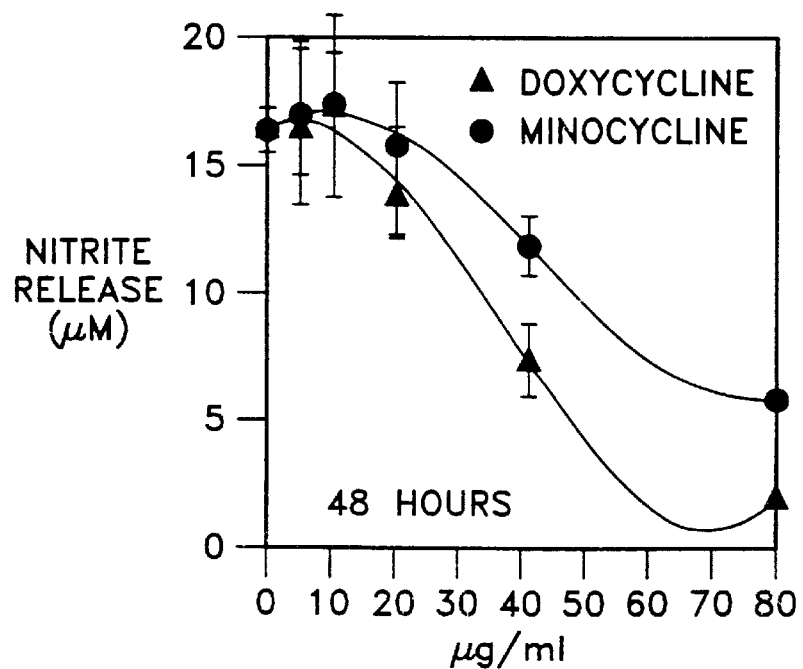
Figure 1C:
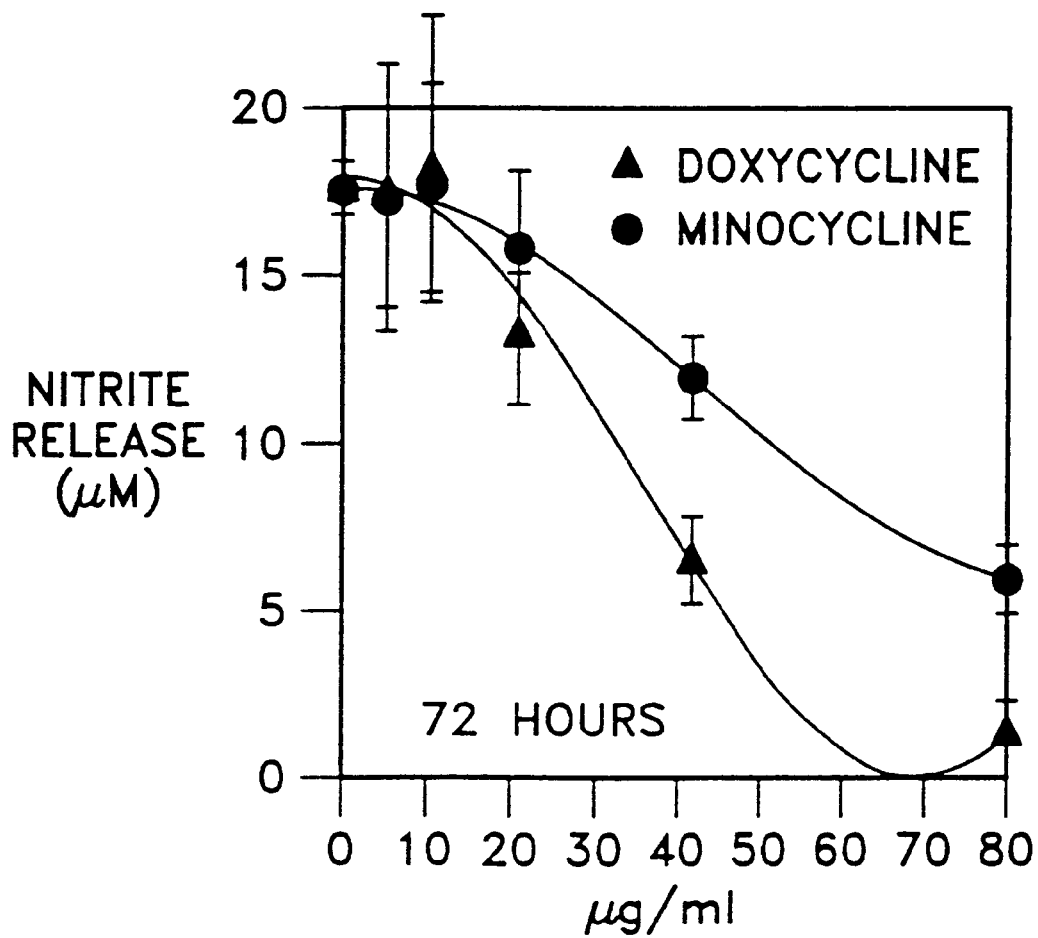

The assay of OA-iNOS in organ culture was basically carried out as described previously (Amin et al. 1995a). Briefly, the OA-affected cartilage was cultured in the presence or absence (Control) of doxycycline and minocycline at 5–80 μg/mL, for 24–72 h in an incubator (37° C.). Activity of NOS was monitored at different time intervals by estimating the amount of the stable end-product, nitrite, in the medium by a modified Griess reaction (Gilliam et al. 1993) using an ELISA reader. The amount of NO spontaneously released (as measured by nitrite accumulation) at 0, 24, 48 and 72 h was 0, 4.8±0.38, 16.4±0.7, and 17.8±0.9 μM, respectively. Data are expressed as μM nitrite released± (SD), n=3–4. The statistics were derived using unpaired Student's test. FIGS. 1A–1C show a time series of graphs (1A=24 h; 1B=48 h; and 1C=72 h) summarizing data representing one of three identical experiments with samples from different patients.

The results shown in FIGS. 1A–1C indicate that doxycycline and minocycline each significantly inhibited NO production in OA-affected cartilage in a dose-dependent manner. These data also indicate that doxycycline was more potent in its ability to inhibit OA-NOS activity. For example, at 72 h, the $IC_{50}$ for doxycycline was 32 μg/mL compared to 54 μg/mL for minocycline. These experiments further indicate that doxycycline and minocycline not only blocked the ongoing production of NO by OA-NOS ex vivo, but also caused a decline in nitrite accumulation in cartilage organ culture for at least 72 h under conditions in which nitrite continues to accumulate in control cultures. The concentrations of doxycycline that inhibited NO production in our studies are comparable to those required for the inhibition of matrix metalloproteinases (Greenwald 1994, Yu et al. 1991, Cole et al. 1994, Mallya et al. 1994). Matrix metalloproteinase inhibitors have a profound effect on cartilage degradation (Cole et al. 1994, Mitchell et al. 1994). The effect of 20–50 μg/mL doxycycline, which interferes with cartilage degradation by inhibiting the activity of proteolytic enzymes such as collagenase and gelatinase, also in turn blocks proteoglycan loss and reduces the cell death associated with proteoglycan loss (Cole et al. 1994).

EXAMPLE 3
Effects of Tetracyclines on iNOS in Murine Macrophages

Our recent studies have indicated that human inducible OA-NOS is distinct from murine and human iNOS, based upon its size, immunoreactivity and susceptibility to TGF-β and hydrocortisone (Amin et al. 1995a). Therefore, we also evaluated the effect of tetracyclines on the production of NO by iNOS in stimulated murine macrophages.

Figure 2A:
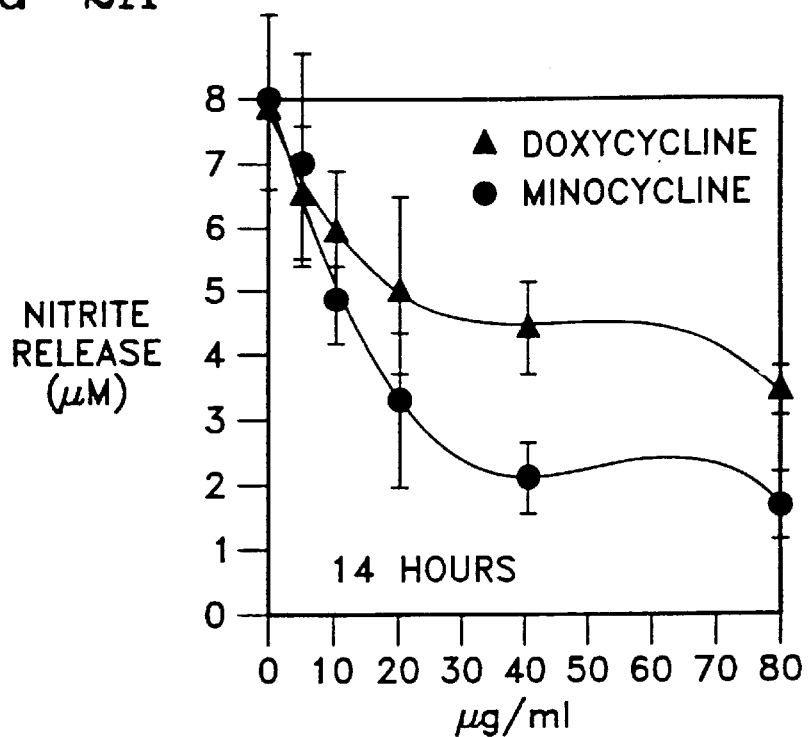
FIGS. 2A–2B are a time series of graphs illustrating dose-dependent inhibition of nitric oxide production in murine macrophages (RAW 264.7 cells) in cell culture by doxycycline and minocycline.
Figure 2B:
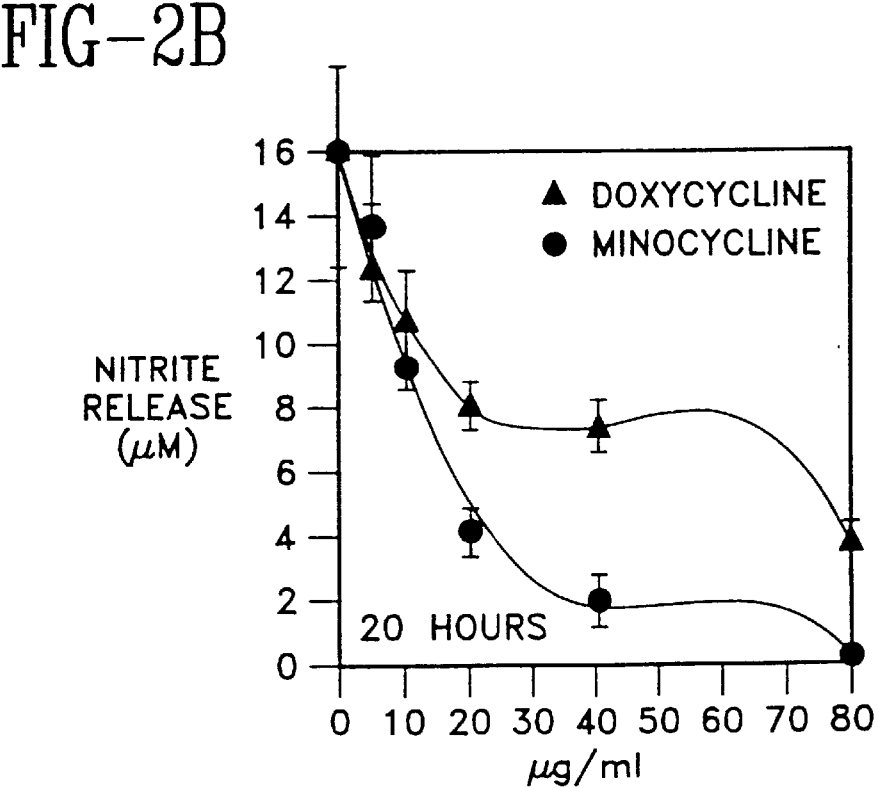

RAW 264.7 murine macrophage cells (American Type Culture Collection, Rockville, Md.) were incubated with and without doxycycline or minocycline (5–80 μg/mL) for 1–2 h followed by activation through addition of 100 ng/mL of LPS (Sigma Chemical Co., St. Louis, Mo.) to induce iNOS (Stuehr et al. 1991). After 14–20 h of incubation, the medium was used to estimate nitrite accumulation by the modified Griess reaction (Gilliam et al. 1993). Data are shown in FIGS. 2A–2B. The values are represented as μM of nitrite accumulated at a given time interval; n=3. The statistics were derived using unpaired Student's t test. The data represent one of three similar experiments.

FIGS. 2A–2B show a concentration-dependent inhibition of nitrite accumulation in cells stimulated with LPS in the presence of 5–80 μg/mL of doxycycline at 14 h (FIG. 2A) and 20 h (FIG. 2B) of incubation. The $IC_{50}$ of (oxycycline in this experiment was 72 μg/mL at 14 h and 22 μg/mL at 20 h of incubation in these cells. In the same set of experiments minocycline was also administered at concentrations ranging from 5–80 μg/mL. The $IC_{50}$ for minocycline was 17 μg/mL at 14 h and 12 μg/mL at 20 h of incubation in RAW 264.7 cells stimulated with LPS. Although no significant difference in the potency of doxycycline and minocycline was seen at 20 h of incubation (based on $IC_{50}$s), significantly higher concentrations of doxycycline, as compared to minocycline, were required to inhibit iNOS-mediated production of NO by >50% at both time intervals.

Examples 2 and 3, above, indicate that both doxycycline and minocycline inhibit NO production both in OA-affected articular cartilage and in murine macrophages stimulated with LPS. Furthermore, these experiments show that the iNOS and inducible OA-NOS have distinct susceptibility to doxycycline, minocycline, in addition to the known susceptibility of these enzymes to TGF-β and hydrocortisone (Amin et al. 1995a). In view of this observation is interesting to note that two different forms of collagenase, MMP-8 ($IC_{50}$ 7–15 μg/mL) and MMP-1 ($IC_{50}$ 140 μg/mL), in two different cell types (i.e., neutrophils and fibroblasts) show distinct susceptibility to tetracyclines (Suomalainen et al. 1992). Furthermore, it should be noted that the same enzyme expressed in two closely related cell lines can have differential susceptibility to tetracyclines. For example, in two osteoblastic cell lines, UMR 106-01 ($IC_{50}$>200 μg/mL) and ROS 17/2.8 ($IC_{50}$=20–30 μg/mL), showed differential susceptibility to doxycycline when evaluated for gelatinase activity (Vernillo et al. 1993). Another factor that may contribute to the differential $IC_{50}$s of tetracyclines on NOS activity in cartilage slices and macrophage cells may be due to the property of these drugs to penetrate the cartilage and act on chondrocytes (Gilman et al. 1993).

EXAMPLES 4–6

Based on the above Examples 2 and 3, we sought to further elucidate the mechanism of action of tetracyclines on NOS expression in the murine macrophage model. This model was used since: (a) the biochemistry, enzymology and molecular biology of iNOS is well characterized in these cells (Nathan et al. 1994, Stuehr et al. 1991, Salvemini et al. 1993, Xie et al. 1994); (b) the differential susceptibility of iNOS to doxycycline and minocycline could shed light on the action of two closely related compounds; and (c) our inability, after several attempts, to precisely and reproducibly quantitate the expression of OA-NOS directly from the OA-affected cartilage without disturbing the architecture of the cartilage, which plays a significant role in chondrocyte function.

Using RAW 264.7 induced cells, we examined the following hypotheses. Tetracyclines may (i) decrease only the catalytic activity of iNOS without influencing the expression of iNOS protein; (ii) decrease both the catalytic activity of iNOS and the expression of iNOS protein, which in turn cumulatively leads to decrease in the accumulation of nitrite in the medium; or (iii) decrease the expression of iNOS protein, and therefore decrease the specific activity of the enzyme and subsequently the production of nitrite.

To test these alternative hypotheses, we examined the action of doxycycline and minocycline on (i) the catalytic activity of iNOS in cell-free extracts, (ii) the specific activity of the enzyme, (iii) the synthesis of iNOS at the protein level, and (iv) the accumulation of iNOS mRNA. These experiments are described in Examples 4–6, below.

EXAMPLE 4A

Effect of Tetracyclines on the Catalytic Activity of iNOS

Murine macrophage cells (RAW 264.7) were incubated with 20–80 µg/mL doxycycline or minocycline, 10 µM hydrocortisone (Sigma Chemical Co., St. Louis, Mo.), or 75 µM L-NMMA for 1–2 h, followed by addition of LPS at 100 ng/mL and incubation for 16–18 h. Cell-free extracts were prepared at the end of each time period. Specific activity of iNOS was determined in the cell-free extracts by monitoring the conversion of L-[$^3$H]-arginine to L-[$^3$H]-citrulline as described by Amin et al. (1995b) and Vyas et al. (1996).

Cell-free extracts were prepared as follows: Following induction by incubation with LPS, the cells were pelleted at 4° C. and resuspended in Tris buffer (10 mM, pH 7.4) containing 10 µg/mL each chymostatin, antipain, leupeptin and pepstatin, 1 mM DTT and 1 mM PMSF. Cells were lysed in a Polytron PT 1200 homogenizer (Kinematica AG, Switzerland) after 3 cycles of rapid freeze-thawing. The lysate was centrifuged at 16,000 rpm for 60 min at 4° C., and the supernatants were used as cell-free extracts.

The protein in the extracts was measured by BCA assay reagent using BSA as standard (Smith et al. 1985). The reaction mixture for iNOS assay consists of Tris 50 mM (pH 7.8); BSA 1 mg/mL; DTT 1 mM; $CaCl_2$, 2 mM; FAD 10 µM; $BH_4$ 10 µM; L-arginine 30 µM; NADPH 1 mM. The reaction mixture was spiked with 1 µL (250 nM) of L-[$^3$H]-arginine (Dupont NEN, Boston, Mass.) (1 mCi/mL=37.0 MBq/mL). After 20 min the assays were terminated by heating the reaction mixture at 90° C. for 5 min. Ten microliters (≅100,000 cpm) of the supernatant was spotted on activated AVICEL TLC plates (Analtech, Newark, Del.). The TLC plates were developed in a solvent system consisting of ethanol:water:ammonia (80:16:4). Quantitation of the spot for L-[$^3$H]-citrulline was performed by a Bioscan System 200 Imaging Scanner.

Figure 3:
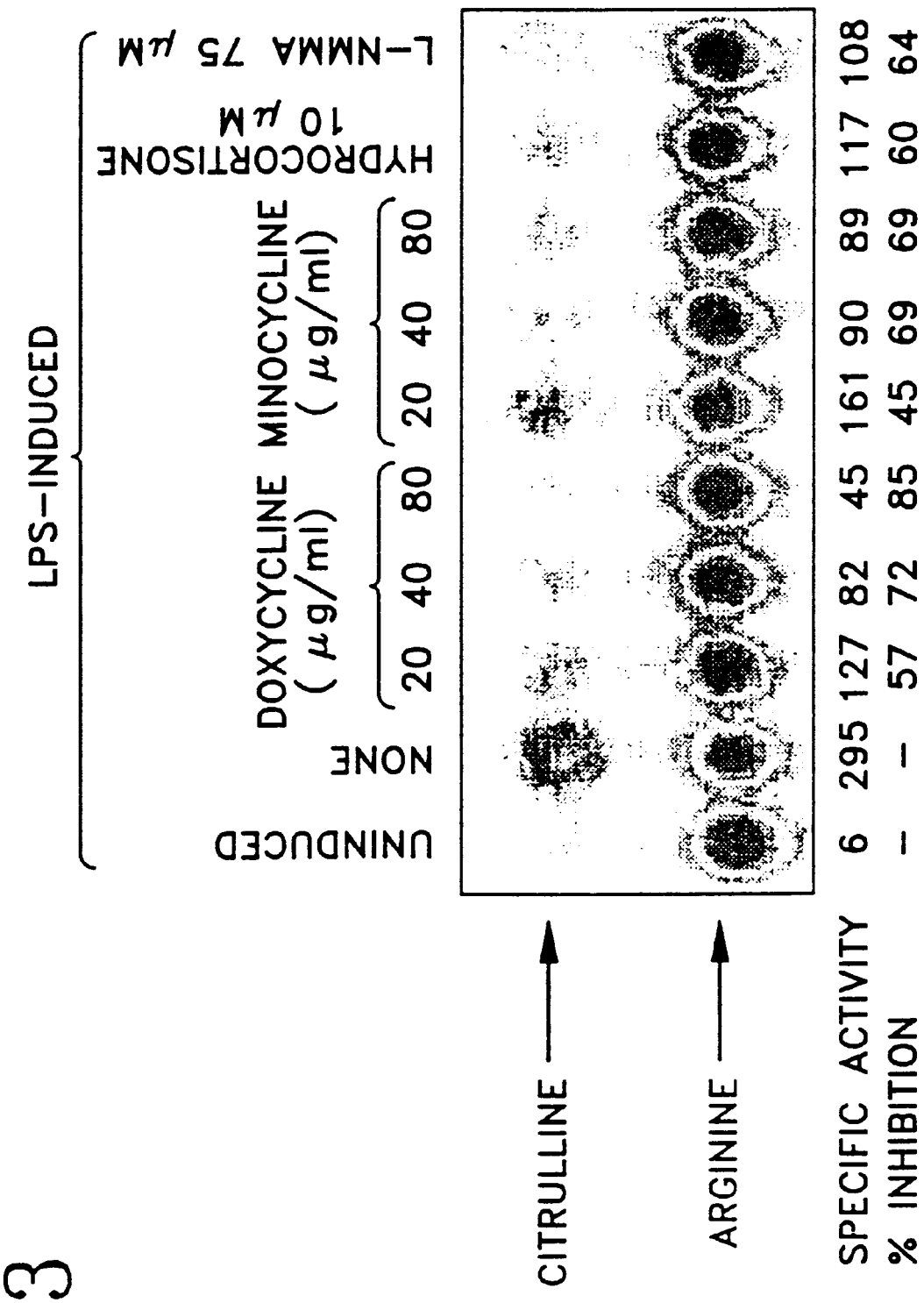
FIG. 3 is a scanned image of a thin layer chromatography (TLC) plate showing dose-dependent reduction in L-[$^3$H]-arginine to L-[$^3$H]-citrulline conversion by murine macrophage cell stimulated (by LPS) to produce iNOS.

FIG. 3 shows the specific activity of the iNOS enzyme under the various experimental conditions, represented as pmol citrulline/min/mg protein. The % inhibition represents comparison against the LPS-stimulated cells in the absence of any modulator. The data represent one of three similar experiments. As shown in FIG. 3, exposure of murine macrophages to either doxycycline or minocycline inhibits the catalytic activity of iNOS in cell lysates in a dose-dependent manner when compared to the control LPS-stimulated activity. Doxycycline at 20, 40 and 80 µg/mL significantly blocks iNOS activity, by 57%, 72% and 85%, respectively; minocycline at the same concentrations also blocks iNOS activity, by 45%, 69% and 69%, respectively. As expected, the positive controls, 10 µM hydrocortisone, and 75 µM L-NMMA, block iNOS activity by 60% and 64%, respectively. The $IC_{50}$ for doxycycline and minocycline to inhibit iNOS activity in cell lysates was ~20–30 µg/mL.

EXAMPLE 4B

Effect of Tetracyclines on the Specific Activity of iNOS In Vitro

Recent studies have indicated that doxycycline inhibits collagenase activity via direct effects on the enzyme (Yu et al. 1991, Smith et al. 1994). One of the mechanisms proposed is that procollagenase is reduced to inactive fragments upon activation in the presence of doxycycline. We have recently shown that acetylating agents, such as aspirin and N-acetyl imidazole (Amin et al. 1995b), as well as competitive inhibitors of L-arginine (Schmidt et al. 1994, Nathan et al. 1994, Marletta 1994) inhibit iNOS catalytic activity in vitro. To evaluate the direct effect of doxycycline and minocycline on iNOS activity, we induced RAW 264.7 cells with LPS for 16 h in the absence of these agents and prepared cell-free extracts as a source of iNOS enzyme in the L-arginine-to-L-citrulline conversion assay.

Separate aliquots of the enzyme-containing cell-free extracts were preincubated for 15 min with 20–80 µg/mL doxycycline, 20–80 µg/mL minocycline, 1 mM N-acetylimidazole and 200 µM L-NMMA, respectively, before the enzyme reaction was initiated by adding the co-factors. Various modulators including methanol (MeOH), the carrier for NAI (N-acetylimidazole), were added 15 min prior to the addition of the co-factors to initiate the iNOS reaction, as described. The specific activity was calculated and percent inhibition was compare to the original LPS-stimulated extract; 100% specific activity was 200 pmol citrulline/min/mg protein. The data shown in FIG. 4 represent one of two similar experiments.

Figure 4:
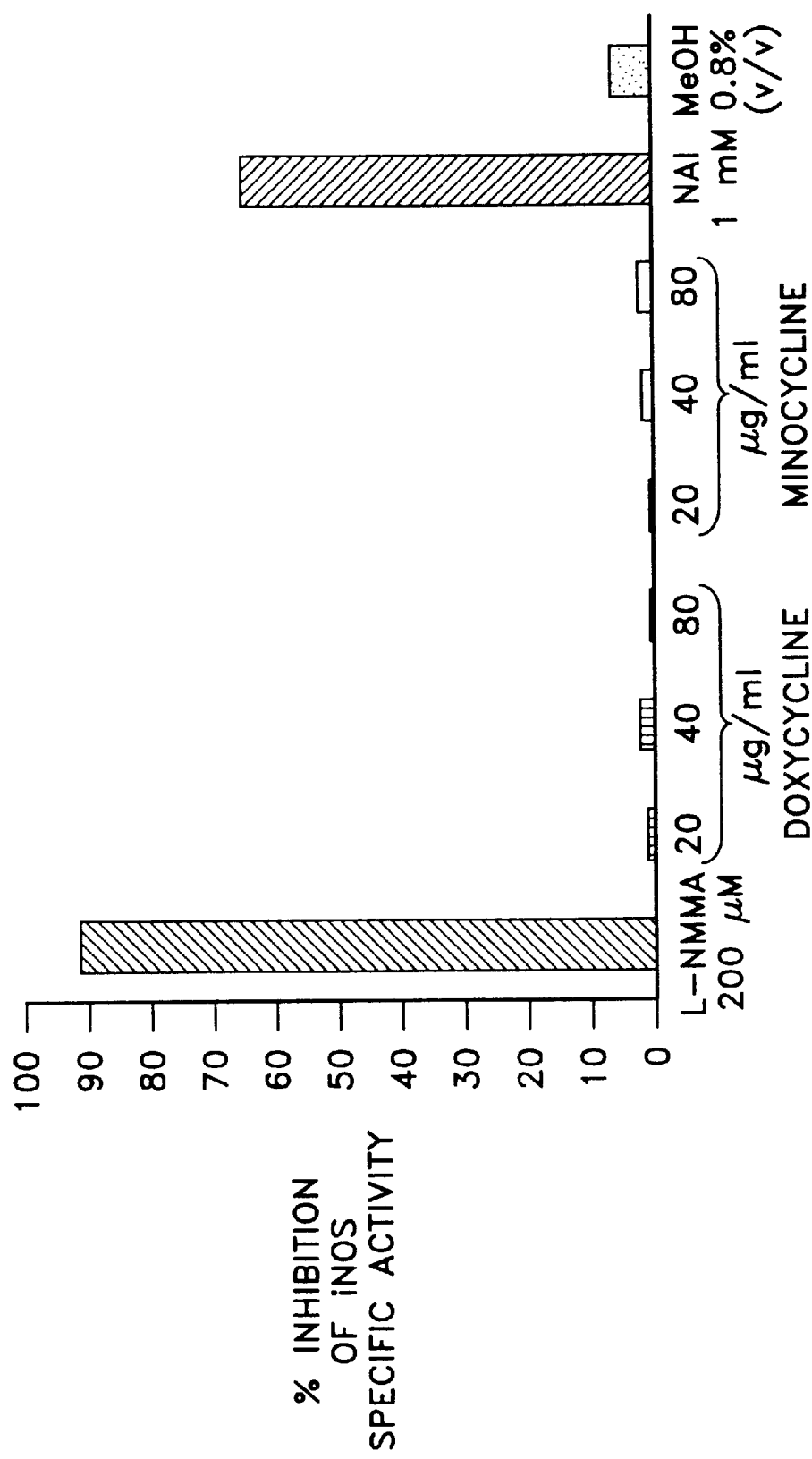
FIG. 4 is a histogram chart showing that doxycycline and minocycline have minimal effect on the specific activity of iNOS in LPS-stimulated murine macrophages in vitro.

FIG. 4 shows that, unlike N-acetyl imidazole or L-NMMA, doxycycline and minocycline had no significant effect on the specific activity of iNOS in cell-free extracts. Minocycline and doxycycline could not block an ongoing L-arginine-to-L-citrulline reaction catalyzed by iNOS in cell-free extracts. These experiments indicate that the action of these drugs on iNOS seems to be distinct from that reported for metalloproteinases such as procollagenases (Yu et al. 1991, Smith et al. 1994).

EXAMPLE 5
Effect of Tetracyclines on iNOS Protein Expression in Murine Macrophages Based on the above data, which indicated that tetracyclines did not directly affect the activity of iNOS, we proceeded to examine iNOS protein expression. RAW 264.7 cells were activated with 100 ng/mL LPS for 16–18 h, with and without doxycycline or minocycline (20–80 $\mu$g/mL) or with hydrocortisone (10 $\mu$M). Cell-free extracts were prepared as described above. The extracts were analyzed for 133 kD iNOS by Western blotting, using specific anti-iNOS antibodies.

Figure 5:
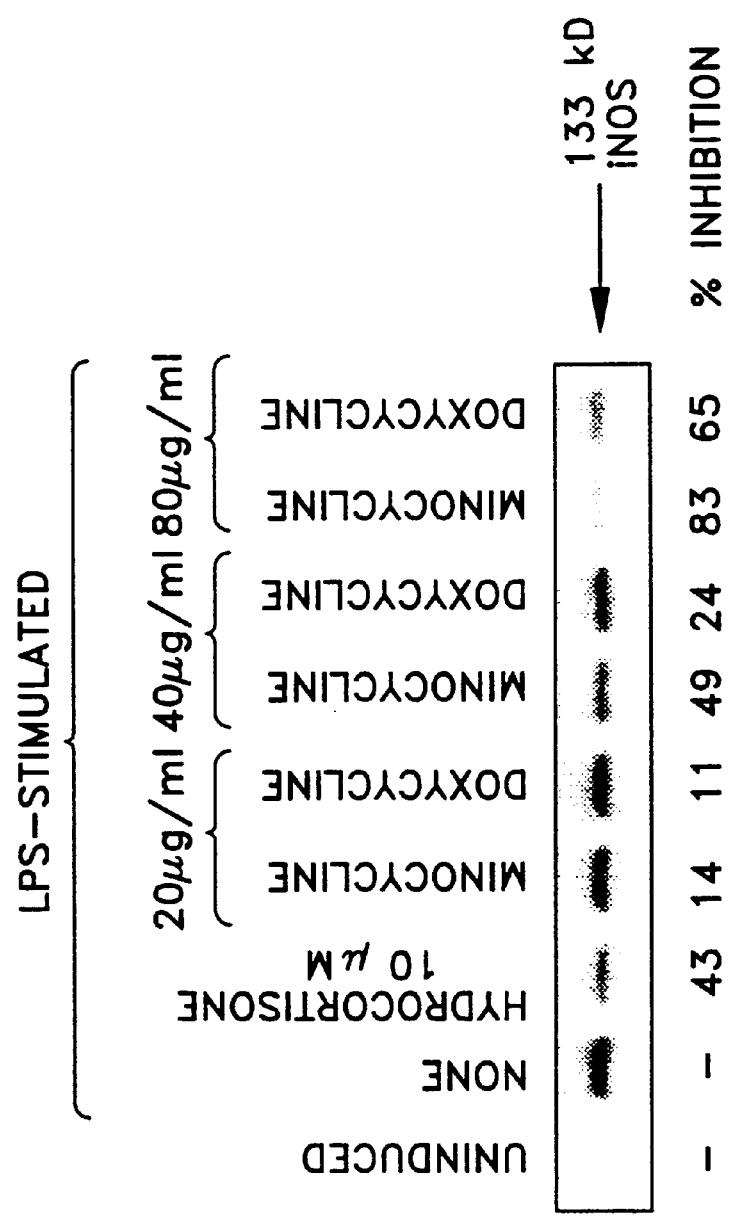
FIG. 5 is a densitometric scan of a Western blot showing a dose-dependent inhibition by doxycycline and minocycline on iNOS expression by LPS stimulated murine macrophages in vitro.

Equal amounts of protein (25–50 $\mu$g) estimated by BCA reagent (Pierce, Rockford, Ill.) were loaded onto SDS-PAGE gels and stained to verify the concentrations of various protein fractions by examining the intensities of the protein bands on the gels. Western blot analysis was carried out from the same cell extracts. The Western-blotted membrane was probed with a specific anti-murine iNOS monoclonal antibody (Transduction Laboratories, Lexington, Ky.), as specified by the supplier. The same blot was also probed with an anti-actin antibody generously provided by Dr. James L. Lessard (Children's Hospital Medical Center, Cincinnati, Ohio). The blots were developed using the ECL Western blot system (Amersham, Arlington Heights, Ill.). Quantitation of the bands was performed using a densitometer from Molecular Dynamics (Sunnyville, Calif.). FIG. 5 is representative.

FIG. 5 shows a dose-dependent inhibition of iNOS protein expression in the presence of both doxycycline (11% at 20 $\mu$g/mL; 24% at 40 $\mu$g/mL; 65% at 80 $\mu$g/mL) and minocycline (14% at 20 $\mu$g/mL; 49% at 40 $\mu$g/mL; 83% at 80 $\mu$g/mL). By comparison, the positive control, hydrocortisone, gave 43% inhibition. (The data represent one of four similar experiments). There was no significant effect on the levels of $\beta$-actin synthesis in the same samples treated with doxycycline or minocycline at 20–80 $\mu$g/mL (data not shown), thus indicating that the effects of doxycycline and minocycline on iNOS are specific.

It should be noted that the $IC_{50}$s for the inhibition of nitrite accumulation and protein expression for each tetracycline derivative were similar, consistent with the thesis that the inhibition of protein expression accounted for the inhibition of NOS activity. Indeed, since both drugs inhibited iNOS protein expression but failed to block the L-arginine-to-L-citrulline conversion in cell-free extracts, we conclude that decrease in catalytic activity of iNOS, which is principally due to inhibition of iNOS protein expression, accounts for the decreased accumulation of nitrite in cells treated with doxycycline and minocycline.

EXAMPLE 6A
Effect of Tetracyclines on the Expression of iNOS mRNA

Doxycycline and minocycline may suppress iNOS before the synthesis of the enzyme, leading to inhibition of iNOS protein expression, specific activity and accumulation of nitrite. This assumption is based on the observation that, in macrophages, TGF-$\beta$1, cyclosporin, hydrocortisone, NF-$\kappa$B inhibitors and to some extent $Fe^{++}$ suppress iNOS expression by decreasing mRNA expression and subsequently the rate of translation of iNOS protein (Nathan et al. 1994, Vodovotz et al. 1993). In addition, recent studies by Pfeilschifter et al. (1995) have shown that dexamethasone acts at multiple levels (including transcription of iNOS) to suppress IL-1$\beta$-induced iNOS expression in mesangial cells. Therefore, to determine the level at which tetracycline inhibited iNOS protein expression, RAW 264.7 cells treated with LPS in the presence or absence of doxycycline and minocycline were analyzed for iNOS mRNA by semi-quantitative RT-PCR.

The presence of iNOS and $\beta$-actin mRNA in cells was analyzed by reverse transcription (RT) of total RNA followed by PCR amplification of the cDNA. The sense and antisense oligonucleotides for iNOS were, respectively, 5'-ACG GAG AAG CTT AGA TCT GGA GCA GAA GTG-3' (142 to 171) (SEQ ID NO:1) and 5'-CTG CAG GTT GGA CCA CTG GAT CCT GCC GAT-3' (767 to 796) (SEQ ID NO:2). The sense and antisense primers for $\beta$-actin were 5'-TCC TTC GTT GCC GGT CCA CA-3' (44 to 63) (SEQ ID NO:3) and 5'-CGT CTC CGG AGT CCA TCA CA-3' (534 to 552) (SEQ ID NO:4), respectively. The predicted PCR product of the iNOS cDNA was 654 bp; that of the $\beta$-actin cDNA was 508 bp. The polymerase chain reaction was carried out in an automated DNA thermal cycle (Perkin-Elmer Cetus, Norwalk, Conn.). The total RNA was extracted using TRI-Reagent (MRC Inc., Cincinnati, Ohio). The cDNA was prepared from equal amounts (1–5 $\mu$g) of total RNA using a SuperScript™ RNase H Reverse Transcriptase (Gibco BRL, Gaithersburg, Md.). An equal amount of the cDNA was used to amplify the mRNA by PCR. PCR amplification was performed in 50 $\mu$L solution containing 1.5 mM $MgCl_2$, 500 ng iNOS primer, 100 ng $\beta$-actin primer, 0.2 mM of each dNTP, 2.5 units of Taq DNA polymerase (Gibco). The cycle conditions for amplification of cDNA were 1 min at 94° C., 1–2 min at 55° C. and 3 min at 72° C. for 30 cycles for both iNOS and $\beta$-actin. The PCR product was analyzed by electrophoresis on 1.0% agarose gels.

RT-PCR analysis of iNOS and $\beta$-actin mRNA expression in RAW 264.7 cells was carried out after stimulation with LPS±doxycycline or minocycline. RAW cells were stimulated with LPS in the presence and absence of doxycycline/ minocycline or 10 $\mu$M hydrocortisone. Equal amounts of RNA were analyzed for iNOS and $\beta$-actin expression as described above.

Figure 6A:
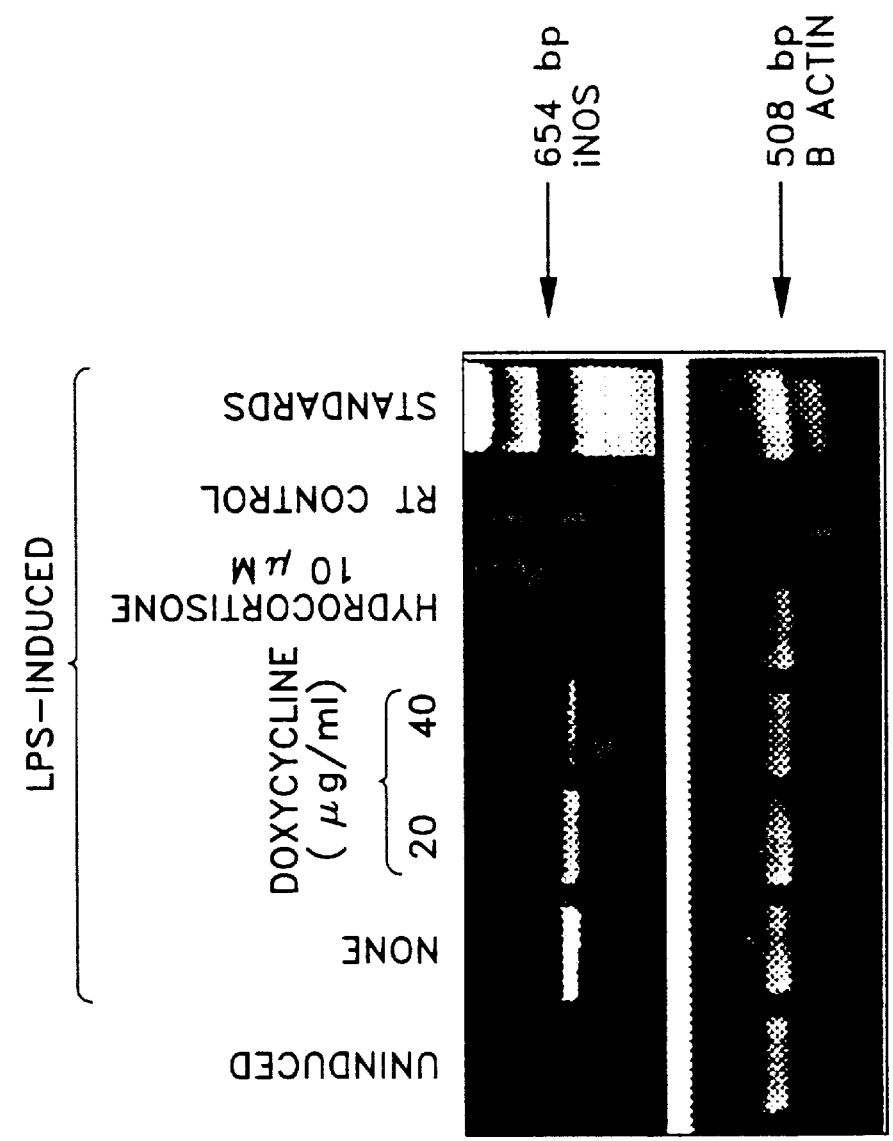
FIGS. 6A and 6B are images of electrophoretic separations of mRNA produced by RT-PCR, showing specific and dose-dependent inhibition of iNOS mRNA synthesis in LPS-stimulated macrophages by doxycycline (FIG. 6A) and minocycline (FIG. 6B)
Figure 6B:
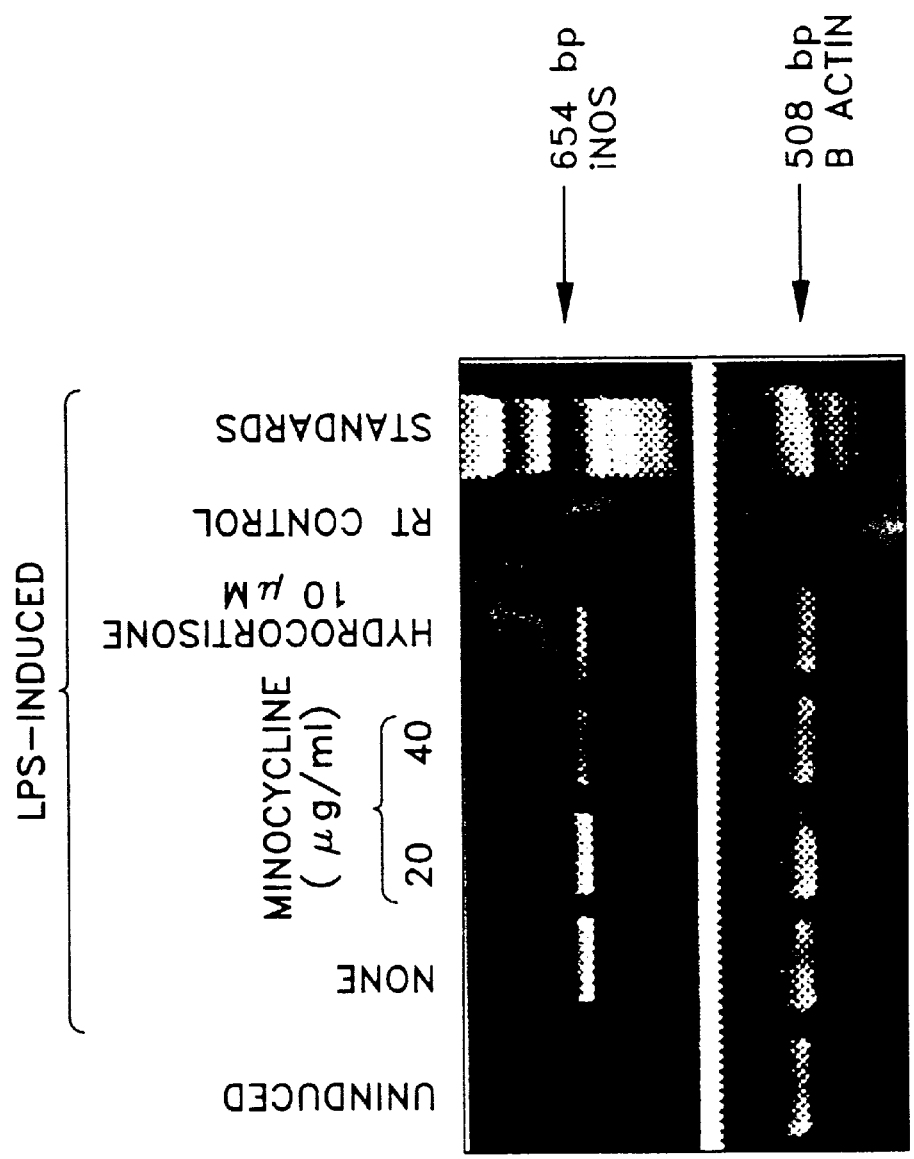

FIGS. 6A and 6B show that doxycycline and minocycline, at concentrations (20–40 $\mu$g/mL) that also inhibited iNOS protein expression, significantly decreased (>50%) iNOS mRNA expression in a dose-dependent fashion. As expected, hydrocortisone-treated cells showed decreased iNOS mRNA (50–100%), as compared to LPS-stimulated cells. "RT-Control" designates preparation of RT-PCR reactions in the absence of reverse transcriptase using the LPS-stimulated RNA as the template from RAW 264.7 cells. The RT-Control samples yielded no mRNA. The data represent one of two similar and separate experiments. The iNOS PCR signals were normalized with $\beta$-actin as shown in FIGS. 6A and 6B.

EXAMPLE 6B
Effect of Tetracyclines on the Expression of iNOS mRNA

In a separate iNOS mRNA isolation procedure identical to that described in Example 6A, RAW cells were stimulated with LPS in the presence and absence of doxycycline and minocycline as well as 10 $\mu$M hydrocortisone. Northern blot analysis of the iNOS mRNA expressed by the cells was then carried out to evaluate precisely the effect of iNOS expression in the presence of doxycycline and minocycline. The probes again were the iNOS and $\beta$-actin cDNA probes described above.

In this case, total RNA was isolated using TRI Reagent (MRC Inc., Cincinnati, Ohio). Northern blot analysis was carried out as described by Church and Gilbert (1984). Briefly, 30 $\mu$g of RNA was subjected to electrophoresis in 1% agarose formaldehyde gel. The gel was then transferred via capillary action onto a nylon membrane (Zeta Probe, Bio-Rad Laboratories, Melville, N.Y.). The membrane was hybridized with [$^{32}$P]-dCTP-labeled iNOS cDNA (4 kb SmaI fragment), a kind gift from Dr. James Cunningham (Harvard Medical School, Boston, Mass.). After hybridization, the blot was exposed to Kodak X-ray film (Kodak, Rochester, N.Y.) for 24–48 h with intensifying screens at −70° C. The β-actin probe was purchased from ClonTech (Palo Alto, Calif.) and probed as described above. Quantitation of the intensity of the iNOS/β-actin bands was performed using a phosphoimager (Molecular Dynamics, Sunnyville, Calif.).

Figure 6C:
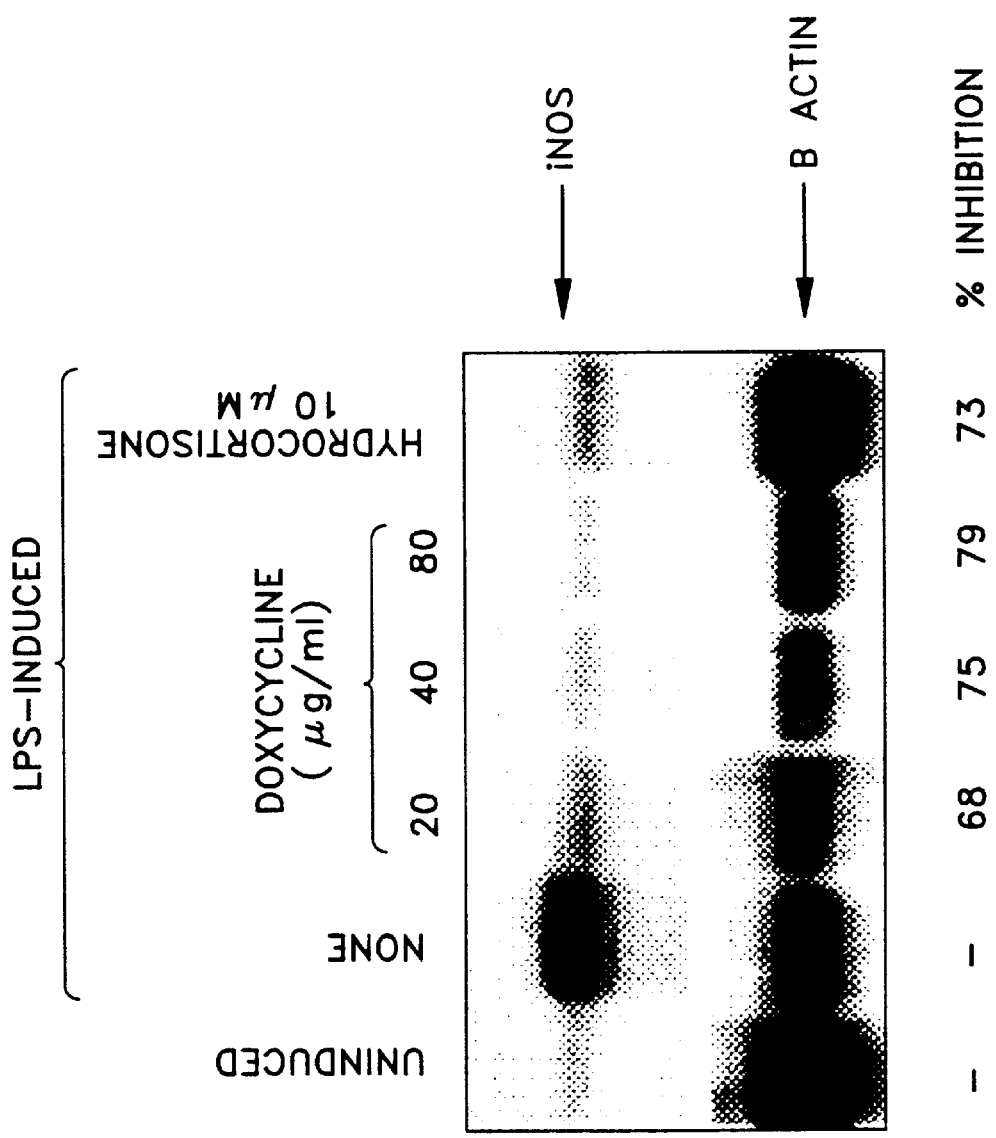
FIGS. 6C and 6D phosphoimager scans of Northern blots showing specific and dose-dependent inhibition of iNOS mRNA synthesis in LPS-stimulated macrophages by doxycycline (FIG. 6C) and minocycline (FIG. 6D).
Figure 6D:
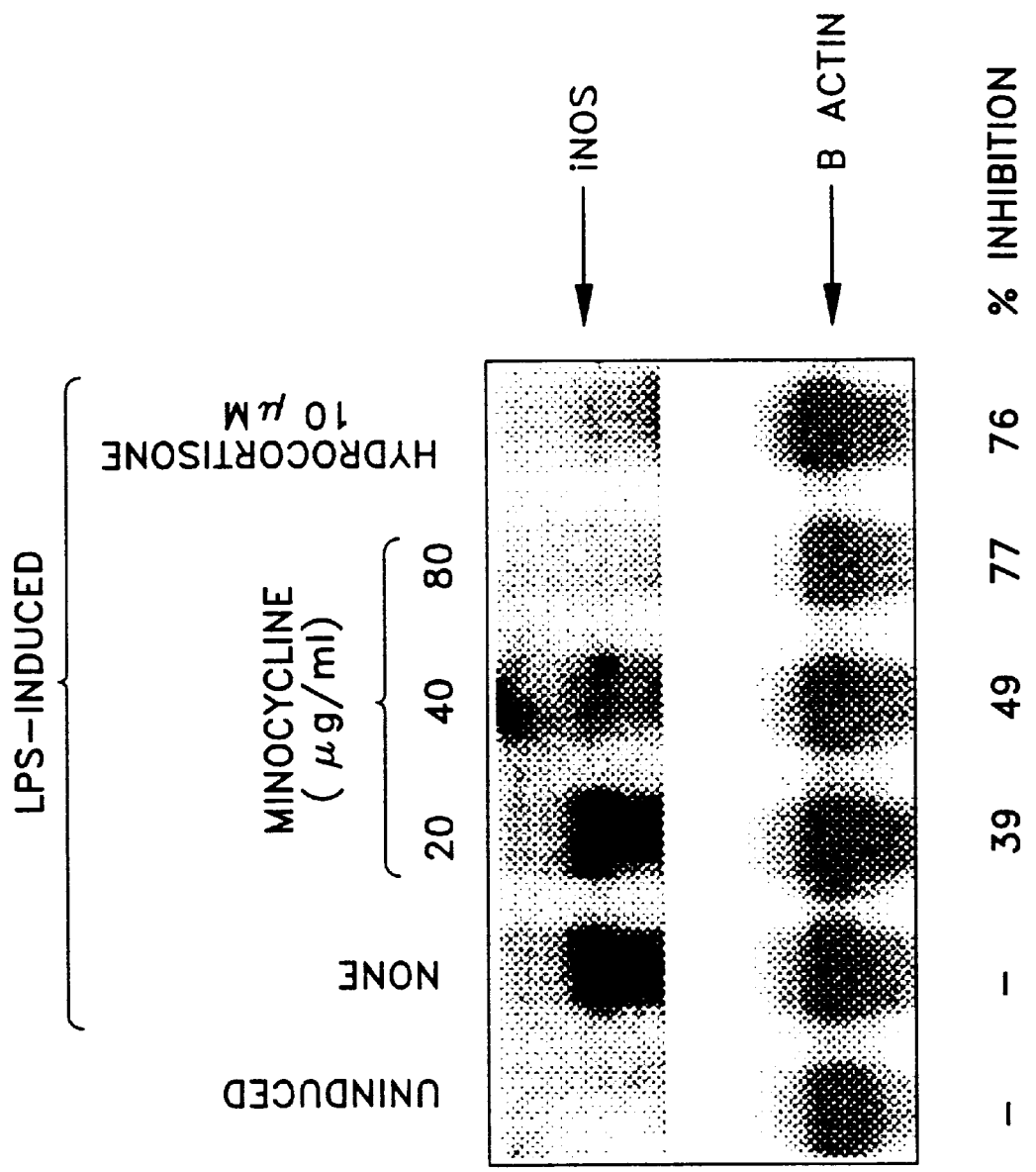

FIGS. 6C and 6D show Northern blots illustrating mRNA expression in the presence and absence of doxycycline (FIG. 6C) and minocycline (FIG. 6D). A dose-dependent inhibition of iNOS mRNA expression is evident in both cases. The percent inhibition of iNOS expression was normalized against the β-actin signal. For doxycycline, the inhibition of mRNA expression was 68% at 20 μg/mL; 75% at 40 μg/mL; and 79% at 80 μg/mL, while hydrocortisone inhibited the expression by 73%. For minocycline, the inhibition of mRNA expression was 39% at 20 μg/mL; 49% at 40 μg/mL; and 77% at 80 μg/mL, while hydrocortisone inhibited the expression by 76%. The data shown in FIGS. 6C–6D represent one of two similar experiments.

Together, Examples 6A and 6B show that 20–40 μg/mL of doxycycline and minocycline significantly blocked iNOS mRNA expression. These experiments indicate that the action of doxycycline and minocycline on iNOS is also at the level of iNOS mRNA expression, which contributes to decreased NOS proteins and specific activity of the enzyme in whole cell extracts. It should be noted that even 80 μg/mL concentration of tetracycline could not completely inhibit iNOS expression at the mRNA level, thus leaving room for some NO production in the presence of these drugs. At this stage of the experiments we do not know if tetracyclines inhibit iNOS transcription or render the iNOS mRNA more susceptible to degradation—or both. It is quite possible that due to the broad spectrum of effects of doxycycline and minocycline on various enzymes and cellular functions, a common target (such as NF-κB) cannot be ruled out. It should be noted that the inhibitory effects of doxycycline/minocycline on iNOS expression (mRNA, specific activity and nitrite accumulation) reach a plateau at ~40–80 μg/mL concentration, beyond which further inhibition of NOS activity has not been achieved. These compounds therefore differ from competitive inhibitors of the enzyme (e.g., L-NMMA), which can inhibit NOS activity >95%. However, tetracyclines at pharmacological concentrations did achieve >50% inhibition of NOS activity in our studies. This is important because even modest effects (10–50%) of NOS inhibition in vivo can have profound attenuating effects on inflammatory events (e.g., paw swelling), as shown in animal models of arthritis (Stefanovic-Racic et al. 1994).

Our data, taken together with previous findings by others, indicate that tetracyclines exert a multiplicity of functions independent of their anti-microbial activity. These functions now include inhibition of NOS expression and NO production, in addition to previously known functions such as inhibition of MMPs, inhibition of tumor progression, inhibition of bone resorption (DeClerck et al. 1994, Rifkin et al. 1994), inhibition of angiogenesis (Maragoudakis et al. 1994) and inhibition of inflammation (Ramamurthy et al. 1994). We speculate that the several properties of tetracyclines (Greenwald et al. 1994) may be partially attributed to their newly discovered ability to target another multifunctional signaling molecule, NO, which is known to exert similar effects on many of the pathological conditions and manifestations listed above (Vane et al. 1994, Schmidt et al. 1994, Murrell et al. 1995, Farias-Eisner et al. 1994, Kasten et al. 1994, Pipili-Synetos et al. 1993, Pipili-Synetos et al. 1994). Our studies also indicate that tetracyclines, at similar $IC_{50}$s, exert dual effects on the MMPs: (a) inhibition of the specific activity of MMPs at the enzyme level (Yu et al. 1991, Smith et al. 1994); and (b) inhibition of NO production, which has been reported to upregulate MMP activity (Murrell et al. 1995). In addition, since NO is known to mediate several catabolic activities of IL-1 on cartilage (Taskiran et al. 1994, Cao et al. 1996, Murrell et al. 1995), the inhibition of NOS activity by tetracyclines may therefore exert additional protective effects on cartilage degradation in arthritis.

Our studies indicate that the tetracyclines inhibit iNOS activity not via a direct inhibition at the enzyme level (as reported for the metalloproteinases) but through an inhibition of NOS mRNA expression, which leads to the decrease in protein expression and NOS activity. This unique property of the tetracycline group of compounds makes them promising candidates as safe and acceptable modulators of NO for various pathological conditions.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

Amin, A. R., Di Cesare, P., Vyas, P., Attur, M., Tzeng, E., Billiar, T. R., Stuchin, S. A. & Abramson, S. B. (1995a) *J. Exp. Med.* 182, 2097–2102.

Amin, A. R., Vyas, P., Attur, M., Leszczynska-Piziak, J., Patel, I. R., Weissman, G. & Abramson, S. B. (1995b) *Proc. Natl. Acad. Sci. USA* 92, 7926–2930.

Brinckerhoff, C. E. (1991) *Arthritis Rheum.* 34, 1073–1075.

Cao, M., Westerhausen-Larson, A., Niyibizi, C., Kavalkovich, K., Georgescu, H. I., Rizzo, C. F., Stefanovic-Racic, M. & Evans, C. H. (1996) *42nd Ann. Mtg. Orthoped. Res. Soc.*, p. 533.

Chandrasoma & Taylor (1991) *Concise Pathology*, 1st ed., Appleton & Lange, pp. 34–44.

Church, G. M. & Gilbert, W. (1984) *Proc. Natl. Acad. Sci. USA* 81, 1991–1995.

Cole, A. A., Chubinskaya, S., Chlebek, K., Orth, M. W., Luchene, L. L. & Schmid, T. M. (1994) *Annals N.Y. Acad. Sci.* 732, 414–415.

Collier et al. (1989) *Trends in Pharmacol. Sci.* 10, 427–431.

Cotran, Kumar & Robbins (1989) *Robbins Pathologic Basis of Diseases*, 4th ed., W. B. Saunders Company, pp. 40–41.

DeClerck, Y. A., Shimada, H., Taylor, S. M. & Langley, K. E. (1994) *Annals N.Y. Acad. Sci.* 732, 222–232.

Farias-Eisner, R., Sherman, M. P., Aeberhard, E. & Chaudhuri, G. (1994) *Proc. Natl. Acad. Sci. USA* 91, 9407–0411.

Gilliam, M. B., Sherman, M. P., Griscavage, J. M. & Ignarro, L. J. (1993) *Anal Biochem.* 212 (2), 359–365.

Gilman, A. G., Rall, T. W., Nies, A. S. & Taylor, P., eds. (1993) *Goodman and Gilman's The Pharmacological Basis of Therapeutics*, 8th ed. (McGraw-Hill, New York).

Golub, L. M., Ramamurthy, N. S. & McNamara, T. F. (1991) *Crit. Rev. Oral Biol. Med.* 2, 297–322.

Golub, L. M., Sorsa, T. & Suomalainen, K. (1992) *Curr. Opin. Dent.* 2, 80–90.

Greenwald, R. A. (1994) *Annals N.Y. Acad. Sci.* 732, 181–198.

Greenwald, R. A. & Golub, L. M., eds. (1994) Inhibition of Matrix Metalloproteinases: Therapeutic Potential. *Annals N.Y. Acad. Sci.* Vol. 732, 1–507.

Kasten, T. P., Colin-Osdoby, P., Patel, N., Osdoby, P., Krukowski, M., Misko, T. P., Settle, S. L., Currie, M. G. & Nickols, G. A. (1994) *Proc. Natl. Acad. Sci. USA* 91, 3569–3573.

Mallya, S. K., Hall, J. E., Lee, H. M., Roemer, E. J., Simon, S. R. & Golub, L. M. (1994) *Annals N.Y. Acad. Sci.* 732, 303–314.

Maragoudakis, M. E., Peristeris, P. Missirlis, E., Aletras, A., Andriopoulou, P. & Haralabopoulos, G. (1994) *Annals N.Y. Acad. Sci.* 732, 280–293.

Marletta, M. A. (1994) *Cell* 78, 927–930.

McCartney-Francis, N., Allen, J. B., Mizel, D. E., Albina, J. E., Xie, Q. W., Nathan, C. F. & Wahl, S. M. (1993) *J. Exp. Med.* 178, 749–754.

Mitchell, P. G., Lopresti-Morrow, L., Yocum, S. A., Sweeney, G. J. & Reiter, L. A. (1994) *Annals N.Y. Acad. Sci.* 732, 395–397.

Mitscher, L. A. (1978) *The Chemistry of the Tetracycline Antibiotics*, Ch. 6, Marcel Dekker, New York.

Mohtai, M., Smith R. L., Schurman, D. J., Taub, Y., Torti, F. M., Hutchinson, N. I., Stetler-Stevenson, W. G. & Goldberg, G. I. (1993) *J. Clin. Inv.* 92, 179–185.

Murrell, G. A. C., Jang, D. & Williams, R. J. (1995) *Biochem. Biophys. Res. Comm.* 206, 15–21.

Nathan, C. & Xie, Q. (1994) *Cell* 78, 915–918.

Pfeilschifter, J., Walker, G., Eberhardt, W. & Kunz, D. (1995) *Endothelium* 3 (suppl.), S51.

Pipili-Synetos, E., Sakkoula, E., Haralabopoulos, G., Andriopoulou, P., Peristeris, P. & Maragoudakis, M. E. (1994) *Br. J. Pharmacol.* 111, 894–902.

Pipili-Synetos, E., Sakkoula, E. & Maragoudakis, M. E. (1993) *Br. J. Pharmacol.* 108, 855–857.

Ramamurthy, N., Greenwald, R., Moak, S., Scuibba, J., Goren, A., Turner, G., Rifkin, B. & Golub, L. (1994) *Annals N.Y. Acad. Sci.* 732, 427–430.

Rifkin, B. R., Vernillo, A. T., Golub, L. M. & Ramamurthy, N. S. (1994) *Annals N.Y. Acad. Sci.* 732, 165–180.

Sakurai, H., Kohsaka, H., Liu, M. F., Higashiyama, H., Hirata, Y., Kanno, K., Saito, I. & Miyasaka, N. (1995) *J. Clin. Inv.* 96, 2357–2363.

Salvemini, D., Misko, T. P., Masferrer, J. L., Seibert, K., Currie, M. G. & Needleman, P. (1993) *Proc. Natl. Acad. Sci. USA* 90, 7240–7244.

Schmidt, H. H. H. W & Walter, U. (1994) *Cell* 78, 919–925.

Smith, G. N., Jr., Brandt, K. D. & Hasty, K. A. (1994) *Annals N.Y. Acad. Sci.* 732, 436–438.

Smith, P. K., Krohn, R. I., Hermanson, G. T., Mallia, A. K., Gartner, F. H., Provenzano, M. D., Fujimoto, E. K., Goeke, N. M., Olson, B. J. & Klenk, D. B. (1985) *Anal. Biochem.* 150, 76–85.

Stefanovic-Racic, M., Meyers, K., Meschter, C., Coffey, J. W., Hoffman, R. A. & Evans, C. H. (1994) *Arthritis Rheum.* 37, 1062–1069.

Stuehr, J. D., Cho, H. J., Kwon, N. S., Weiss, M. S. & Nathan, C. F. (1991) *Proc. Natl. Acad. Sci. USA* 88, 7773–7777.

Suomalainen, K., Sorsa, T., Golub, L. M., Ramamurthy, N., Lee, H. M., Uitto, V. J., Saari, H. & Konttinen, Y. T. (1992) *Antimicrob. Agents Chemother.* 36, 227–229.

Taskiran, D., Stefanovic-Racic, M., Georgescu, H. & Evans, C. E. (1994) *Biochem. Biophys. Res. Comm.* 200, 142–148.

Tilley B C, Alarcon G S, Heyse S P, Trentham D E, Neuner R, Kaplan D A, Clegg D O, Leisen J C C, Buckley L, Cooper S M, Duncan H, Pillemer S R, Tuttleman M, Fowler S E. Minocycline in rheumatoid arthritis. *Ann. Intern. Med.* 122:81–89 (1995).

Uitto, V. J., Firth, J. D., Nip, L. & Golub, L. M. (1994) *Annals N.Y. Acad. Sci.* 732, 140–151.

Vane, J. R., Mitchell, J. A., Appleton, I., Tomlinson, A., Bishop-Bailey, D., Croxtall, J. & Willoughby, D. A. (1994) *Proc. Natl. Acad. Sci. USA* 91,2046–2050.

Vernillo, A. T., Ramamurthy, N. S., Lee, H. M., Mallya, S., Auszmann, J., Golub, L. M. & Rifkin, B. R. (1993) *J. Dent. Res.* 73, 367A.

Vodovotz, Y., Bogdan, C., Paik, J., Xie, Q. W. & Nathan, C. (1993) *J. Exp. Med.* 178, 605–613.

Vyas, P., Attur, M., Ou, G. M., Haines, K. A., Abramson, S. B. & Amin, A. R. (1996) In *The Biology of Nitric Oxide*, Part 5. Moncada, S., Stamler, J., Gross, S., and Higgs, E. A. (eds.) Portland Press Proceedings, p. 44.

Xie, Q. W., Kashiwabara, Y. & Nathan, C. (1994) *J. Biol. Chem.* 269, 4705–4708.

Yu, L. P., Jr., Smith, G. N., Jr., Hasty, K. A. & Brandt, K. D. (1991) *J. Rheumatol.* 18, 1450–1452.

Yu, L. P., Jr., Smith, G. N., Jr., Brandt, K. D. Myers, S. L., O'Connor, B. L. & Brandt, D. A. (1992) *Arthritis Rheum.* 35, 1150–1159.

---

What is claimed is:

1. A method of inhibiting expression of inducible nitric oxide synthase in a mammal system, comprising administering to said mammal system an amount of a tetracycline compound sufficient to inhibit inducible nitric oxide synthase expression in said mammal system.

2. The method according to claim 1, wherein the tetracycline compound has substantially no anti-microbial activity in said mammal system.

3. The method according to claim 1, wherein the tetracycline compound has metalloproteinase inhibitory activity.

4. The method according to claim 1, wherein the tetracycline compound is 6-demethyl-6-deoxy-4-dedimethylaminotetracycline (CMT-3), 6-α-deoxy-5-hydroxy-4-dedimethylaminotetracycline (CMT-8), 4-dedimethylaminotetracycline (CMT-1), doxycycline, or minocycline.

5. The method according to claim 1, wherein said mammal system is a mammal having a condition characterized by increased nitric oxide production.

6. The method according to claim 5, wherein said mammal has nitric oxide-dependent glomerular inflammation.

7. The method according to claim 5, wherein said mammal has osteoarthritis.

8. The method according to claim 1, wherein said method further comprises providing to said mammal system an anti-inflammatory amount of a steroidal or non-steroidal anti-inflammatory drug.

9. The method according to claim 1, wherein said mammal system is a mammal having a condition characterized by an abnormally high level of activity of inducible nitric oxide synthase.

10. The method according to claim 1, wherein said mammal system is an in vitro cellular system or an ex vivo tissue or organ system wherein a measured amount of nitric oxide production is indicative of expression of inducible nitric oxide synthase.

* * * * *